(12) United States Patent
Braenden et al.

(10) Patent No.: US 8,692,014 B2
(45) Date of Patent: Apr. 8, 2014

(54) ACID ADDITION SALTS OF 5-AMINOLEVULINIC ACID OR ITS DERIVATIVES

(75) Inventors: Jon Erik Braenden, Oslo (NO); Aslak Godal, Oslo (NO); Nils Olav Nilsen, Oslo (NO); Jo Klaveness, Oslo (NO)

(73) Assignee: Photocure ASA, Oslo (NO)

( * ) Notice: Subject to any disclaimer, the term of this patent is extended or adjusted under 35 U.S.C. 154(b) by 831 days.

(21) Appl. No.: 12/916,326

(22) Filed: Oct. 29, 2010

(65) Prior Publication Data

US 2011/0125012 A1    May 26, 2011

Related U.S. Application Data

(62) Division of application No. 10/594,361, filed as application No. PCT/GB2005/001236 on Mar. 29, 2005, now Pat. No. 7,888,526.

(30) Foreign Application Priority Data

Mar. 26, 2004 (GB) .................................. 0406917.5

(51) Int. Cl.
*C07C 229/00* (2006.01)
*A61K 31/195* (2006.01)

(52) U.S. Cl.
USPC .......................................... 560/155; 514/506

(58) Field of Classification Search
None
See application file for complete search history.

(56) References Cited

U.S. PATENT DOCUMENTS

| 5,284,973 | A  | 2/1994  | Ebata et al.     |
| 5,298,482 | A  | 3/1994  | Tanaka et al.    |
| 5,489,572 | A  | 2/1996  | Yoshida et al.   |
| 5,661,111 | A  | 8/1997  | Kuramochi et al. |
| 5,907,058 | A  | 5/1999  | Moens            |
| 6,034,267 | A  | 3/2000  | Gierskcky et al. |
| 7,217,736 | B2 | 5/2007  | Klaveness et al. |
| 7,287,646 | B2 | 10/2007 | Gierskcky et al. |

FOREIGN PATENT DOCUMENTS

| CA | 2 417 533 A1 | 2/2002 |
| CA | 2 454 136 A1 | 2/2003 |
| EP | 0-483 714    | 5/1992 |
| EP | 0 607 952    | 7/1994 |
| EP | 0995448      | 4/2000 |
| JP | 4-9360       | 1/1992 |
| JP | 4338305      | 11/1992 |
| JP | 7-53311      | 2/1995 |
| JP | 7-238063     | 9/1995 |
| JP | 8-151304     | 6/1996 |
| JP | 11-12197     | 1/1999 |
| WO | WO 91/01727  | 2/1991 |
| WO | WO 96/28412  | 9/1996 |
| WO | WO 02/10120  | 2/2002 |
| WO | WO-2005/100300 | 10/2005 |

OTHER PUBLICATIONS

Van den Bergh, "Light and porphyrins in cancer therapy," Chemistry in Britain, May 1986, p. 430-439.
Woodford et al., "Penetration Enhancers and the Percutaneous Absorption of Drugs: An Update," J, Toxicol. Cut. & Ocular Toxicology, 1986, 5: 167-177.
Azone®, Stoughton et al., "Enhancer of Cutaneous Penetration," Drug Dpv. Ind. Pharm. 1983, 9: 725-744.
O'Reilly et al., "Angiostatin induces and sustains dormancy of human primary tumors in mice," Nature Medicine, 2, p. 689-692, 1996.
Yamamoto et al., Significant Inhibition of Endothelial Cell Growth in Tumor Vasculature by an Angiogenesis Inhibitor, TNP-470 (AGM-1470), Anticancer Research, 14, p. 1-4, 1994.
Brooks et al., "Antiintegrin $\alpha v \beta 3$ blocks human breast cancer growth and angiogenesis in human skin," J. Clin. Invest., 96, p. 1815-1822, 1995.
Baxter et al., "Evidence for Specific Lead-δ-aminolevulinate Complex Formation by Carbon-13 Nuclear Magnetic Resonance Spectroscopy," Toxicology and Applied Pharmacology 47, pp. 477-482 (1979).
Berge et al, "Potentially Useful Salts," Journal of Pharmaceutical Sciences, vol. 66, No. 1, Jan. 1977, pp. 1-19.
Japanese Office Action (translated) dated Feb. 22, 2011 issued for corresponding JP Patent Application No. 2007-504487, 4 pages.
Mar. 23, 2011 letter from Louise Golding of Dehns showing listing of foreign document equivalents.

Primary Examiner — Yevegeny Valenrod
(74) Attorney, Agent, or Firm — Kenyon and Kenyon LLP

(57) ABSTRACT

The present invention provides an acid addition salt of 5-aminolevulinic acid (5-ALA) or of a 5-ALA derivative (e.g. a 5-ALA ester) with an acid which has a pKa of about 5 or less, preferably about 3 or less, with the proviso that the acid is other than hydrochloric acid. Particularly preferred salts are those derived from acids selected from the group comprising sulphonic acid and its derivatives, hydrobromic acid, sulfuric acid, nitric acid and phosphoric acid. The salts in accordance with the invention are particularly suitable for use as photosensitizing agents in diagnosis and photochemotherapy of disorders or abnormalities of external or internal surfaces of the body.

24 Claims, 6 Drawing Sheets

ACID ADDITION SALTS OF 5-AMINOLEVULINIC ACID OR ITS DERIVATIVES

CROSS-REFERENCE TO RELATED APPLICATIONS

This application is a divisional of prior U.S. patent application Ser. No. 10/594,361 filed Aug. 6, 2007 now U.S. Pat. No. 7,888,526, which is a National Phase Application of PCT International Application No. PCT/GB2005/001236 filed on Mar. 29, 2005, and which claims priority to British Patent Application No. 0406917.5 filed Mar. 26, 2004, all of which are hereby expressly incorporated herein by reference in their entirety.

The present invention relates to certain salts of 5-aminolevulinic acid (5-ALA) and its derivatives, their preparation and their use, in particular as photosensitizing agents in photochemotherapy or diagnosis. The invention particularly relates to new salts of 5-ALA and new salts of 5-ALA esters.

Photochemotherapy, or photodynamic therapy (PDT) as it is also known, is a technique for the treatment of various abnormalities or disorders of the skin or other epithelial organs or mucosa, especially cancers or pre cancerous lesions, as well as certain non-malignant lesions, for example skin complaints such as psoriasis. Photochemotherapy involves the application of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished.

A range of photosensitizing agents are known including notably the psoralens, the porphyrins (Photofrin®), the chlorins and the phthalocyanins drugs become toxic when exposed to light.

Amongst the most clinically useful photosense agents known in the art are 5-aminolevulinic acid its derivatives, for example esters such as 5-ALA esters. These are described, for example, in WO91/01727, WO96/28412 and WO02/10120. To date, such compounds have only been proposed for clinical use in the form of their hydrochloride salts, for example as ALA-HCl in Levulan® (available from Dusa Pharmaceuticals Inc., Wilmington, US), as ALA methyl ester HCl in Metvix® (PhotoCure ASA, Oslo, Norway) and as ALA hexyl ester HCl in Hexvix® (also PhotoCure ASA).

Although photochemotherapy with ALA and ALA derivatives is clinically useful in the treatment of a wide range of pre-cancerous and cancerous diseases and other conditions, such compounds nevertheless exhibit some limitations when formulated for use as pharmaceuticals, e.g. in PDT. For example, these compounds (in particular, ALA and its hydrochloride salt) tend to be unstable in pharmaceutical formulations. In some cases, such compounds may also be associated with problems relating to their physicochemical properties, for example their crystalline properties, solubility or hygroscopic properties.

Thus, a need therefore exists for alternative photochemotherapeutic agents. In particular, a need exists for such agents which are better pharmaceuticals, for example photochemotherapeutic agents which have improved physicochemical properties (e.g. which are more stable, less hygroscopic, etc.) compared to those known in the art. It is also desirable that such agents should exhibit equivalent, or preferably, improved efficacy (i.e. an equivalent or enhanced photochemotherapeutic effect) over known photosensitizers when used in PDT.

Surprisingly, it has now been found that certain salts of 5-aminolevulinic acid and its derivatives, in particular salts of ALA esters, possess desirable properties for use in pharmaceutical formulations (e.g. formulations for use in photochemotherapy) and that a number of such salts have improved properties relative to ALA compounds known and used in the art. Specifically, it has been found that acid addition salts of ALA and its derivatives (e.g. ALA esters) with an acid, other than HCl, which has a pKa of about 5 or less, and especially sulfonic acids, are particularly suitable for use in pharmaceutical formulations, e.g. formulations for use in photochemotherapy. For example, such compounds have now been found to possess improved physicochemical properties, such as enhanced stability (e.g. lower hygroscopicity), compared to known ALA compounds. Certain such compounds have also been found to exhibit improved efficacy (i.e. an enhanced photochemotherapeutic effect) over ALA compounds which are presently in clinical use, for example relative to the corresponding hydrochloride salts of ALA and of ALA esters.

Thus, viewed from one aspect the invention provides an acid addition salt of 5-aminolevulinic acid (5-ALA) or of a 5-ALA derivative (e.g. a 5-ALA ester) with an acid which has a pKa of about 5 or less, with the proviso that the acid is other than hydrochloric acid.

In a preferred embodiment the invention provides acid addition salts of 5-aminolevulinic acid (5-ALA) or its derivatives (e.g. salts of 5-ALA esters) with an acid which has a pKa of less than about 3. Particularly preferred examples of such acids include sulfonic acid and sulfonic acid derivatives.

Preferably, the acid addition salts in accordance with the invention are pharmaceutically acceptable. Thus, it is preferred that the acid from which the salts of the invention are derived should themselves be pharmaceutically acceptable.

In a further aspect the invention also provides such compounds (i.e. acid addition salts) for use as pharmaceuticals, e.g. pharmaceuticals for use in photochemotherapy or diagnosis.

As used herein, the terms "5-aminolevulinic acid", "ALA" and "5-ALA" are used interchangeably and encompass 5-amino-4-oxopentanoic acid. When used in relation to ALA, the term "derivatives" includes chemically modified compounds, for example esters such as ALA esters. Such compounds are typically formed by modification of the 5-ALA carboxylic acid group. The term "derivatives" is also intended to encompass any 5-aminolevulinic acid compound wherein the 5-amino group may be substituted or unsubstituted. In other words, the term "derivatives" used in relation to 5-ALA includes compounds wherein, chemical modification occurs at either or both of the carboxylic acid or 5-amino group of ALA. Derivatives of 5-ALA are generally known and described in the prior art, e.g. in WO96/28412 and WO02/10120, the entire contents of which are incorporated herein by reference. Preferred derivatives of 5-ALA for use in the invention are ALA esters', especially those esters of 5-ALA compounds in which the 5-amino group is unsubstituted.

As used herein, the term "sulfonic acid" is intended to include any organic compound containing at least one —$SO_3H$ group. Preferably, this may comprise 1, 2 or 3 —$SO_3H$ groups, most preferably 1 or 2, e.g. 1. When used in relation to sulfonic acid, the term "derivatives" is intended to encompass any such compounds containing at least one (preferably 1, 2 or 3, most preferably 1 or 2, e.g. 1) —$SO_3X$ group (where X is a physiologically tolerable cation, such as a sodium, calcium, potassium, magnesium or meglumine cation).

Salts according to the invention will typically be derived from ALA or an ALA derivative and a mono-protic acid, e.g.

a sulfonic acid such as methanesulfonic acid, thereby forming a 1:1 salt. Alternatively, salts may be formed between ALA or an ALA derivative and a di- or tri-protic acid, e.g. a sulfonic acid such as ethane-1,2-disulfonic acid, sulfuric acid or phosphoric acid. In the case where an acid having more than one acidic proton is used, the resulting compound may have a stoichiometric ratio other than 1:1, for example 2:1 (ALA:acid) or 3:1 (ALA:acid), or may comprise a mixture of salts having varying levels of stoichiometry. In the case of sulfuric acid, for example, a 2:1 (ALA:acid) salt may form whereas in the case of phosphoric acid a 3:1 (ALA:acid) salt may form. Polyprotic acids are also capable of forming other salts with ALA or an ALA derivative. Sulfuric acid, for instance, may provide a 1:1 (ALA:acid) salt based on the $HSO_4^-$ anion and phosphoric acid may provide both a 2:1 (ALA:acid) and 1:1 (ALA:acid) salt (or combination thereof) based on the $HPO_4^{2-}$ and $H_2PO_4^-$ anions, respectively. Moreover, polyprotic acids can also form other salts, e.g. 1:1 salts, with ALA dr its derivatives (e.g. with ALA esters) in the form of salts with other physiologically acceptable bases, such as sodium hydroxide, calcium hydroxide, potassium hydroxide and meglumine.

Salts according to the invention preferably derive from an acid having a pKa of about 4 or less, more preferably about 3 or less. The acid may be inorganic or organic. Preferred inorganic acids include hydrobromic acid, sulfuric acid, phosphoric acid and, in particular, nitric acid. Preferred organic acids include sulfonic acid and sulfonic acid derivatives. Those salts derived from nitric acid, sulfonic acid and sulfonic acid derivatives are especially preferred.

More preferably, the present invention provides compounds of formula I:

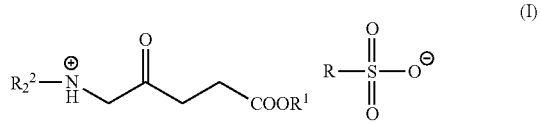

(wherein
R is a hydrogen atom or an optionally substituted alkyl (e.g. a $C_{1-20}$ alkyl group) or aryl group (e.g. an aryl group of up to 20 carbon atoms), preferably an optionally substituted alkyl or aryl group;
$R^1$ and $R^2$ each independently represents a hydrogen atom or an optionally substituted straight-chained, branched or cyclic alkyl group which may optionally be interrupted by one or more —O—, —$NR^3$—, —S— or —$PR^3$— groups; and
$R^3$ is a hydrogen atom or a C alkyl group).

As used herein, unless specifically stated otherwise, the term "alkyl" includes any long or short chain, straight-chained, branched or cyclic aliphatic, saturated or unsaturated hydrocarbon group. Optionally, this group may be substituted (e.g. mono- or poly-substituted), for example by hydroxy, alkoxy, acyloxy, nitro, alkoxycarbonyloxy, amino, aryl, oxo, halo (e.g. fluoro or chloro) groups, —$SR^3$, —$NR^3_2$, or —$PR^3_2$ groups (in which $R^3$ is as hereinbefore defined). The unsaturated alkyl groups may be mono- or polyunsaturated and include both alkenyl and alkynyl groups.

Preferred compounds in accordance with the invention are those of formula I in which R is an optionally substituted (i.e. mono- or poly-substituted), linear, branched or cyclic (e.g. mono- or bicyclic, bridged or non-bridged) alkyl group which may contain up to 20 carbon atoms, or an optionally substituted (i.e. mono- or poly-substituted) aryl group, which preferably contains up to 20 carbon atoms. Preferred substituents which may be present in group R include $C_{1-6}$ alkyl (e.g. methyl), hydroxy, alkoxy, acyloxy, nitro, alkoxycarbonyloxy, amino, aryl, oxo and halo (e.g. fluoro or chloro).

In general, salts according to the invention that are formed between ALA or an ALA derivative and a sulfonic acid compound comprise a single sulfonic acid moiety, i.e. a monoprotic acid. However, as noted above, compounds having more than one sulfonic acid moiety (e.g. 2 or 3 such groups) are contemplated within the scope of the invention. Other substituents which may be present in group R therefore include one or more, preferably one, —$SO_2OH$, —$SO_2OX$ (where X is as hereinbefore defined) or —$SO_2O^\ominus$ group. Representative examples of disulfonic acids which may be used to prepare the salts according to the invention include ethane-1,2-disulfonic acid and napthalene-1,5-disulfonic acid.

In the case of group R, preferred alkyl groups may contain up to 20, but preferably up to 15, e.g. up to 12 carbon atoms. However, alkyl groups containing up to 10, e.g. up to 5, more preferably 1, 2 or 3 carbon atoms are preferred. In particular, linear alkyl groups having up to 10 carbon atoms are preferred, e.g. methyl, ethyl or propyl groups. Although these groups may be substituted or unsubstituted, preferably these will be unsubstituted.

In the case of group R, preferred aryl groups include optionally substituted phenyl or napthyl groups. Preferably the aryl group is substituted, for example by one or more (e.g. by one, two or three) substituents which may include $C_{1-6}$ alkyl groups (preferably $C_{1-4}$ alkyl, e.g. methyl), alkoxy (e.g. methoxy), nitro, halo (e.g. fluoro or chloro), —$SO_2H$, —$SO_3X$ (where X is as hereinbefore defined), —$SO_2O^-$ or trifluoromethyl groups. Representative examples of aryl groups include toluene (e.g. p-toluene), benzene, napthalene and napthalene, sulfonate (e.g. 2-napthalenesulfonate).

In the case of $R^1$ and $R^2$, preferred alkyl groups are those containing up to 20, e.g. up to 10 carbon atoms. In particular, saturated hydrocarbons having up to 10 carbon atoms are preferred, e.g. hexyl, heptyl or octyl groups. Lower alkyls such as methyl, ethyl and propyl may, however, alternatively be used. Suitable alkyl groups may be linear or branched. Representative examples of suitable branched alkyl groups include 2-methylpentyl and 4-methylpentyl. Generally linear, non-branched alkyl groups are preferred.

The substituted alkyl groups may be mono or poly-substituted. Thus suitable groups $R^1$ and $R^2$ include, for example, unsubstituted alkyl, alkoxyalkyl, hydroxyalkoxyalkyl, polyhydroxyalkyl, hydroxy poly alkyleneoxyalkyl, oxaalkyl, polyoxaalkyl and the like.

Preferred substituted alkyl $R^1$ groups include those carrying one or more oxo groups, preferably straight-chained $C_{4-12}$ (e.g. $C_{9-10}$ alkyl) groups substituted by one, two or three (preferably two or three) oxo groups. Examples of such groups include 3,6-dioxa-1-octyl and 3,6,9-trioxa-1-decyl groups.

Particularly preferred substituted alkyl $R^1$ groups which may be present in compounds of formula I include $C_{1-6}$ alkyl, preferably $C_{1-4}$ alkyl, particularly preferably $C_1$ or $C_4$ alkyl (e.g. methyl) substituted (preferably terminally substituted) by an aryl group. Preferred aryl groups include phenyl, diphenyl and monocyclic 5-7 membered, e.g. 5 or 6-membered, heteroaromatics, especially phenyl and such groups may themselves optionally be substituted, for example by one or more (e.g. one or two) $C_{1-6}$ alkyl groups (preferably $C_{1-4}$ alkyl, e.g. methyl), alkoxy (e.g. methoxy), nitro, fluoro, chloro or trifluoromethyl groups. Suitable heteroaromatic groups include those containing at least one heteroatom selected from oxygen, sulphur and nitrogen. A preferred heteroaromatic group is pyridine.

Representative substituted alkyl groups $R^1$ and $R^2$ include alkoxymethyl, alkoxyethyl and alkoxypropyl groups or acyloxymethyl, acyloxyethyl and acyloxypropyl groups, e.g. pivaloyloxymethyl.

Preferred compounds according to the invention include those of formula I wherein $R^1$ and/or $R^2$, preferably $R^1$, represents an unsubstituted alkyl group or an aryl substituted alkyl group (e.g. a benzyl group), in which the aryl group itself may also be substituted as described herein. Especially, $R^1$ is a $C_{1-6}$ alkyl group, e.g. a $C_1$ or $C_6$ alkyl group or a benzyl group, each of which may optionally be substituted. Preferably the $C_1$ or $C_6$ alkyl group and benzyl group are unsubstituted. Particularly preferably such compounds are salts of ALA esters, i.e. $R^1$ is as described above, and at the N-terminal both $R^2$ groups are hydrogen atoms.

Particularly preferred compounds in accordance with the invention are those compounds of formula I in which $R^1$ either represents an unsubstituted alkyl group (e.g. alkyl) or an alkyl group (e.g. $C_{1-2}$ alkyl) substituted by an aryl group (e.g. phenyl) and/or each $R^2$ represents a hydrogen atom.

Most preferred compounds in accordance with the invention are the sulfonic acid salts or sulfonic acid derivative salts of ALA, methyl ALA ester, 1-methylpentyl ALA ester, p-isopropylbenzyl ALA ester, p-methylbenzyl ALA ester, benzyl ALA ester, 2-phenylethyl ALA ester, hexyl ALA ester, cyclohexyl ALA ester, 4-methylpentyl ALA ester, 2-(2-ethoxyethoxy)ethyl ALA ester, p-[tri-fluoromethyl]benzyl ALA ester, p-[t-butyl]benzyl ALA ester, p-nitrobenzyl ALA ester, 1-ethylbutyl ALA ester, 2-methylpentyl ALA ester, 4-phenyl butyl ALA ester, p-fluorobenzyl ALA ester, 3,3-dimethyl-1-butyl ALA ester, 2-fluorobenzyl ALA ester, 2,3,4,5,6-pentafluorobenzyl ALA ester, 4-chlorobenzyl ALA ester, 2-methoxyethyl ALA ester, 3-nitrobenzyl ALA ester, 3,4-[dichloro]benzyl ALA ester, 3,6-dioxa-1-octyl ALA ester, 3-fluorobenzyl ALA ester, 3,6,9-trioxa-1-decyl ALA ester, 3-pyridinyl-methyl ALA ester, 4-biphenyl-methyl ALA ester, 4-methoxy-benzyl ALA ester, 2-methylbenzyl ALA ester, benzyl-5-[(1-acetyloxyethoxy)-carbonyl]amino levulinate, and 3-methylbenzyl ALA ester.

Other preferred compounds in accordance with the invention include the nitric acid salts, hydrobromide salts, phosphoric acid salts, and sulfuric acid salts of the above-mentioned ALA compounds. Most preferred are the sulfonic acid salts, the sulfonic acid derivative salts and the nitric acid salts of such ALA compounds, especially the sulfonic acid salts and the sulfonic acid derivative salts.

Still more preferred compounds in accordance with the invention are the sulfonic acid salts or sulfonic acid derivative salts of ALA, methyl ALA ester, 1-methylpentyl ALA ester, p-isopropylbenzyl ALA ester, p-methylbenzyl ALA ester, benzyl ALA ester, hexyl ALA ester, 4-methylpentyl ALA ester and 2-(2-ethoxyethoxy)ethyl ALA ester.

The nitric acid salts, hydrobromide salts, phosphoric acid salts and sulfuric acid salts of ALA, methyl ALA ester, 1-methylpentyl ALA ester, p-isopropylbenzyl ALA ester, p-methylbenzyl ALA ester, benzyl ALA ester, hexyl ALA ester, 4-methylpentyl ALA ester and 2-(2-ethoxyethoxy)ethyl ALA ester are also preferred compounds of the invention.

Especially preferred compounds of the invention include the acid addition salts of ALA or ALA derivatives (e.g. ALA esters) with nitric acid, sulfuric acid, phosphoric acid, hydrobromic acid or, more particularly, with a sulfonic acid selected from the following:
napthalene-1,5-disulfonic acid,
ethane-1,2-disulfonic acid,
p-toluenesulfonic acid,
methanesulfonic acid,
dodecylsulfonic acid,
napthalene-2-sulfonic acid,
benzenesulfonic acid,
2-hydroxy-ethanesulfonic acid,
ethanesulfonic acid, and
(+)-camphor-10-sulfonic acid.

Particularly preferred salts are those derived from nitric acid or a sulfonic acid listed above. Salts derived from a sulfonic acid listed above (e.g. from methanesulfonic acid, benzenesulfonic acid and p-toluenesulfonic acid) are especially preferred.

Examples of particularly preferred compounds include:
5-amino-4-oxopentanoic acid toluene sulfonate;
hexyl 5-amino-4-oxopentanoate toluene sulfonate;
benzyl 5-amino-4-oxopentanoate toluene sulfonate;
methyl 5-amino-4-oxopentanoate toluene sulfonate;
2-methyl-1-pentyl 5-amino-4-oxopentanoate toluene sulfonate;
4-methyl-1-pentyl 5-amino-4-oxopentanoate toluene sulfonate;
4-methylbenzyl 5-amino-4-oxopentanoate toluene sulfonate;
4-isopropylbenzyl 5-amino-4-oxopentanoate toluene sulfonate;
5-amino-4-oxopentanoic acid methanesulfonate;
hexyl 5-amino-4-oxopentanoate methanesulfonate;
benzyl 5-amino-4-oxopentanoate methanesulfonate;
methyl 5-amino-4-oxopentanoate methanesulfonate;
2-methyl-1-pentyl 5-amino-4-oxopentanoate methanesulfonate;
4-methyl-1-pentyl 5-amino-4-oxopentanoate methanesulfonate;
4-methylbenzyl 5-amino-4-oxopentanoate methanesulfonate;
4-isopropylbenzyl 5-amino-4-oxopentanoate methanesulfonate;
2-(2-ethoxyethoxy)ethyl 5-amino-4-oxopentanoate benzenesulfonate;
benzyl 5-amino-4-oxopentanoate benzenesulfonate;
benzyl 5-amino-4-oxopentanoate 2-hydroxyethanesulfonate;
benzyl 5-amino-4-oxopentanoate (1S)-10-camphorsulfonate;
benzyl 5-amino-4-oxopentanoate 2-napthalenesulfonate;
benzyl 5-amino-4-oxopentanoate nitrate;
benzyl 5-amino-4-oxopentanoate sulfate;
benzyl 5-amino-4-oxopentanoate phosphate;
5-amino-4-oxopentanoic acid hydrobromide; and
benzyl 5-amino-4-oxopentanoic acid hydrobromide.

Especially preferred compounds in accordance with the invention include the sulfonic acid salts of 5-ALA, 5-ALA methyl ester, 5-ALA hexyl ester and 5-ALA benzyl ester (e.g. 5-amino-4-oxopentanoic acid toluene sulfonate; hexyl 5-amino-4-oxopentanoate toluene sulfonate; benzyl 5-amino-4-oxopentanoate toluene sulfonate; methyl 5-amino-4-oxopentanoate toluene sulfonate; 5-amino-4-oxopentanoic acid methanesulfonate; hexyl 5-amino-4-oxopentanoate methanesulfonate; benzyl 5-amino-4-oxopentanoate methanesulfonate; and methyl 5-amino-4-oxopentanoate methanesulfonate). Benzyl 5-amino-4-oxopentanoate nitrate is also an especially preferred compound.

Acids having a pKa of about 5 or leas and which are suitable for use in forming an acid addition salt in accordance with the invention may be an inorganic acid other than HCl or an organic acid. Representative examples of inorganic acids include hydrobromic acid, sulfuric acid, nitric acid and phosphoric acid. Nitric acid is particularly preferred. Representative examples of organic acids include napthalene-1,5-disulfonic acid, ethane-1,2-disulfonic acid, p-toluenesulfonic acid, methanesulfonic acid, dodecylsulfonic acid, napthalene-2-sulfonic acid, benzenesulfonic acid, 2-hydroxy-ethanesulfonic acid, ethanesulfonic acid, and (+)-camphor-10-sulfonic acid.

Preferably the acid having a pKa of about 5 or less is an organic acid. For example, the acid may be an organic acid having a pKa of about 3 to about 5 or an organic acid having a pKa of about 4 or less (e.g. a pKa of about 3 to about 4). Preferred organic acids may have a pKa of about 3 or less.

Representative examples of organic acids having a pKa of about 3 or less include napthalene-1,5-disulfonic acid, ethane-1,2-disulfonic acid, cyclamic acid, p-toluenesulfonic acid, thiocyanic acid, methanesulfonic acid, dodecylsulfonic acid, napthalene-2-sulfonic acid, benzenesulfonic acid, oxalic acid, 2,2-dichloroacetic acid, glycophosphoric acid, 2-hydroxy-ethanesulfonic-1-acid, L-aspartic acid, maleic acid, ethanesulfonic acid, (+)-camphor-10-sulfonic acid, glutamic acid, alginic acid, pamoic acid, 2-oxo-glutaric acid, 1-hydroxy-2-napthoic acid, malonic acid, gentisic acid, salicyclic acid, and tartaric acid.

Representative examples of organic acids having a pKa of about 3 to about 4 include galactoic acid, citric acid, D-glucuronic acid, lactobionic acid, 4-aminosalicyclic acid, glycolic acid, D-glucoheptonic acid, (−)-L-pyroglutamic acid, DL-mandelic acid, (−)-L-malic acid, hippuric acid, D-gluconic acid, DL-lactic acid and oleic acid.

Representative examples of organic acids having a pKa of about 3 to about 5 include benzoic acid, succinic acid, 4-acetamidobenzoic acid, glutaric acid, cinnamic acid, adipic acid, sebaic acid, (+)-camphoric acid, acetic acid, camporic acid, nicotinic acid, isobutyric acid, propionic acid, capric acid, lauric acid, palmitic acid, stearic acid, undecylenic acid and caprylic acid. Those acids disclosed above as having a pKa of about 3 to about 4 may also be included in this group.

The compounds of the invention or for use in the invention may be prepared using standard processes and procedures well-known in the art for salt formation.

Starting materials for preparation of salts according to the invention include ALA and its derivatives, for example ALA esters, which can be reacted with an acid such as a sulfonic acid, e.g. p-toluenesulfonic acid, methanesulfonic acid, etc.

The invention can thus be seen to provide a process for preparing the compounds of the invention, said process comprising reacting 5-aminolevulinic acid or a derivative thereof (e.g. an ALA ester) with an acid (e.g. a sulfonic acid or sulfonic acid derivative).

Alternatively, in order to prepare a salt of an ALA ester in accordance with the invention, a one-pot reaction may be used which involves reaction of 5-aminolevulinic acid, or an esterifiable derivative thereof, with an alkanol or an ester-forming derivative thereof (e.g. with an alkanol) in the presence of an acid, e.g. a sulfonic acid or sulfonic acid derivative. Such a process forms a further aspect of the invention.

More particularly, this aspect of the invention provides a process for the preparation of an acid addition salt as hereinbefore described (e.g. a compound of formula I), said process comprising the step of reacting a compound of formula II:

$$R^2{}_2N\text{—}CH_2COCH_2\text{—}CH_2COY \quad (II)$$

(wherein
Y represents a leaving group, for example a hydroxyl group, a halogen atom or alkoxy group, or COY represents an acid anhydride group, and $R^2$ is as hereinbefore defined) with a compound of formula III:

$$R^1\text{—}OH \quad (III)$$

(wherein $R^1$ is an optionally substituted straight-chained, branched or cyclic alkyl group which may optionally be interrupted by one or more —O—, —S— or —PR$^3$— groups; and $R^3$ is a hydrogen atom or a C alkyl group) in the presence of an acid as hereinbefore defined, e.g. a sulfonic acid of formula IV:

$$R\text{—}SO_2OH \quad (IV)$$

(wherein R is as hereinbefore defined).

Such reactions may conveniently be carried out in a solvent or mixture of solvents such as water, acetone, methanol, ethanol or tetrahydrofuran etc., preferably water at temperatures up to 100° C., preferably at ambient temperature. The conditions for the reactions will depend on the reagents used and the conditions may be chosen such that maximum yield of the salt is obtained.

The compounds of the invention may also be prepared from the corresponding hydrochloride salts, for example using ion-exchange methods or by a "silver-salt" method as outlined below. These methods form further aspects of the present invention.

The ion-exchange method typically involves a first step of passing a solution containing a hydrochloride salt of ALA or of an ALA derivative through an ion-exchange column and a second step of adding the eluate from the column into a solution of an acid (e.g. a sulfonic acid). Any ion exchange resin capable of exchanging Cl⁻ for a basic anion (e.g. a hydroxide ion) may be used. Suitable ion-exchangers include strongly basic anion exchange resins (e.g. Dowex® 11, Amberlyst® A26(OH) and the like). In this method the chloride ions of the hydrochloride salt of ALA or of an ALA derivative are exchanged for basic (e.g. hydroxide) ions during passage through the column. This provides the free base which is then neutralised with an acid (e.g. a sulfonic acid or sulfonic acid derivative), thereby simultaneously forming the corresponding acid (e.g. sulfonic acid) addition salt of ALA or an ALA derivative.

Thus, viewed from a further aspect, the invention provides a process for the preparation of an acid addition salt in accordance with the invention (e.g. a compound of formula I), said process comprising:

(i) contacting a solution comprising a hydrochloride salt of ALA or of an ALA derivative (e.g. a compound of the formula Cl⁻R²₂N⁺H—CH₂COCH₂CH₂CO₂R¹ wherein R¹ and R² are as hereinbefore defined) with a basic anion exchange resin;

(ii) optionally removing said resin; and (iii) mixing the resulting solution with a solution comprising an acid as hereinbefore defined, preferably a sulfonic acid or a sulfonic acid derivative (e.g. a compound of the formula RSO₃H or RSO₃X wherein R and X are as hereinbefore defined).

In the silver salt method a hydrochloride salt of ALA or of an ALA derivative is reacted with the silver salt of an acid (e.g. a sulfonic acid) in a solvent in which AgCl is insoluble (e.g. water). Examples of suitable silver salts include silver methanesulfonate, silver p-toluenesulfonate, silver benzenesulfonate, silver sulfate, silver phosphate, silver nitrate, etc. In this method, silver may be replaced by any other cation which forms an insoluble compound with chloride ions in a solvent in which the hydrochloride salt of ALA or of an ALA derivative and the appropriate acid addition salt (e.g. sulfonic acid salt) are at least partially (e.g. substantially) soluble. For example, a hydrochloride salt of ALA or of an ALA derivative may be reacted with the sodium, potassium, calcium or magnesium salt of a sulfonic acid in a solvent in which NaCl/KCl/CaCl$_2$/MgCl$_2$ is insoluble (e.g. non-aqueous organic solvents).

Thus viewed from a further aspect the invention provides a process for the preparation of a compound in accordance with the invention (e.g. a compound of formula I), said process comprising:

(i) reacting a hydrochloride salt of ALA or of an ALA derivative (e.g. a compound of the formula Cl$^-$R$^2{}_2$N$^+$H—CH$_2$COCH$_2$CH$_2$CO$_2$R$^1$ wherein R$^1$ and R$^2$ are as hereinbefore defined) with a silver salt of an acid as hereinbefore defined, preferably a sulfonic acid (e.g. a compound of the formula RSO$_3$Ag wherein R is as hereinbefore defined) in a solvent in which AgCl is substantially insoluble; and (ii) optionally separating AgCl from the resulting salt (e.g. sulfonic acid salt).

The methods described above are primarily illustrated with reference to the preparation of the acid addition salts of 5-ALA and 5-ALA derivatives with sulfonic acids and sulfonic acid derivatives. However, as would be clear to those skilled in the art, other acid addition salts in accordance with the invention can be made by analogous methods in which the sulfonic acid or derivative thereof is simply replaced by the required acid.

Compounds used as starting materials are known from the literature, and in many cases are commercially available, or may be obtained using methods known per se. ALA, for example, is available from Sigma. Methods for the preparation of ALA derivatives, e.g. ALA esters, are described for example in WO96/28412 and WO02/10120, the contents of which are incorporated herein by reference.

Some examples of hydrochloride salts well known in the prior art and suitable for use as starting materials for synthesis of acid addition salts (e.g. sulfonic acid salts) according to the present invention include: ALA HCl, methyl ALA ester HCl, hexyl ALA ester HCl, etc.

As mentioned above, the compounds of the invention and for use according to the invention have valuable pharmacological properties, namely as inducers of intracellular porphyrins with photosensitizing properties which renders them useful as photochemotherapeutic agents. However, the compounds of the invention have a number of advantages over known salts of ALA and ALA esters, e.g. the hydrochloride salts. Firstly, the compounds of the invention are generally more stable and less hygroscopic; this has the advantage of long term storage of pharmaceutical preparations without any significant degradation of the active substance which could lead to loss of efficacy. Secondly, certain acid addition salts of the invention, in particular the nitric acid addition salts and the sulfonic acid addition salts, have surprisingly been found to have improved photosensitizing properties; fluorescence levels following administration of the nitric acid or sulfonic acid salts are higher than with the corresponding hydrochloride salts.

A further aspect of the present invention accordingly provides a pharmaceutical composition comprising an acid addition salt of the invention, together with at least one pharmaceutical carrier or excipient.

In a further aspect, there is provided a pharmaceutical composition, as described hereinbefore, for use as a medicament, e.g. in photochemotherapy or diagnosis.

In a still further aspect, there is also provided the use of an acid addition salt of the invention for the preparation of a therapeutic agent for use in photochemotherapy, and especially for the treatment of disorders or abnormalities of external or internal surfaces of the body which are responsive to photochemotherapy.

The abnormalities and disorders which may be treated according to the present invention include any malignant, pre-malignant and non-malignant abnormalities or disorders responsive to photochemotherapy e.g. basal cell carcinoma (bcc), tumours or other growths, skin disorders such as psoriasis or actinic keratoses and acne, skin abrasions, and other diseases or infections e.g. bacterial, viral or fungal infections, for example Herpes virus infections. The invention is particularly suited to the treatment of diseases, disorders or abnormalities where discrete lesions are formed to which the compositions may be directly applied (lesions is used here in a broad sense to include tumours and the like).

The internal and external body surfaces which may be treated according to the invention include the skin and all other epithelial and serosal surfaces, including for example mucosa, the linings of organs eg. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue eg. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining, of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made accessible to photoactivating light e.g. either directly, at time of surgery, or via an optical fibre inserted through a needle.

The compositions of the invention may be formulated in any conventional manner with one or more physiologically acceptable carriers or excipients, according to techniques well known in the art. Where appropriate, compounds or compositions according to the invention are sterilized, e.g. by γ-irradiation, autoclaving or heat sterilization, before or after the addition of a carrier or excipient where that is present, to provide sterile formulations.

Compositions may be administered topically, orally or systemically. Topical compositions are preferred, and include gels, creams, ointments, sprays, lotions, salves, sticks, soaps, powders, pessaries, aerosols, drops, solutions and any of the other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration, for example by intradermal, subcutaneous, intraperitoneal or intravenous injection. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The compositions may additionally include lubricating agents, wetting agents, emulsifying agents, suspending agents, preserving agents, sweetening agents, flavouring agents, adsorption enhancers, e.g. surface penetrating agents as mentioned below, and the like. The compositions of the invention may be formulated so as to provide quick, sustained or delayed release of the active ingredient after administration to the patient by employing procedures well known in the art. Solubilizing and/or stabilizing agents may also be used, e.g. cyclodextrins (CD) α, β, γ and HP-β cyclodextrin. Compositions may be in any appropriate dosage form, for example as an emulsion or in liposomes, niosomes, microspheres, nanoparticles or the like. The compound of the invention may then be absorbed to, incorporated in or bound to these forms.

The concentration of the compounds of the invention in the compositions, depends upon the nature of the compound, the composition, mode of administration, the condition to be treated and the patient and may be varied or adjusted according to choice. Generally however, concentration ranges of 0.01 to 50%, e.g. 0.05 to 20%, e.g. 1-10% (w/w) are suitable. For therapeutic applications concentration ranges of 0.1 to 50% have been found to be suitable, e.g. 0.2 to 30% (w/w). Lower doses may be used when the compounds are highly lipophilic, e.g. in a concentration range of 0.01 to 10%, e.g. 0.02 to 1% (w/w).

Topical administration to inaccessible sites may be achieved by techniques known in the art, e.g. by the use of catheters or other appropriate drug delivery systems.

Following administration to the surface, the area treated is exposed to light to achieve the photo-chemotherapeutic effect. The length of time following administration, at which the light exposure takes place will depend on the nature of the composition, the condition to be treated and the form of administration. This can generally be in the order of 0.5 to 48 hours, e.g. 1 to 10 hours.

The irradiation will in general be applied at a dose level of 40 to 200 Joules/cm$^2$, for example at 100 Joules/cm$^2$.

The wavelength of light used for irradiation may be selected to achieve an efficacious photochemo-therapeutic effect. Irradiation with white light, particularly light having wavelengths in the range 300-800 nm, for example, in the range 500-700 nm has been found to be effective. It may be particularly important to include the wavelengths 630 and 690 nm.

A further aspect of the invention thus provides a method of photochemotherapeutic treatment of disorders or abnormalities of external or internal surfaces of the body, comprising administering to the affected surfaces, an acid addition salt or composition as hereinbefore defined, and exposing said surfaces to light (e.g. white light), preferably to light in the wavelength region 300-800 nm (e.g. blue light in the wavelength region 380-440 nm). Alternatively, light in the wavelength region 500-700 nm may be used.

Methods for irradiation of different areas of the body, e.g. by lamps or lasers are well known in the art (see for example Van den Bergh, Chemistry in Britain, May 1986 p. 430-439). For inaccessible regions this may conveniently be achieved using optical fibres.

The compounds of the invention may be formulated and/or administered with other photosensitizing agents, for example Photofrin®, or with other active components which may enhance the photochemotherapeutic effect. For example, chelating agents may beneficially be included in order to enhance accumulation of the potent photosensitizer protoporphyrin IX (Pp); the chelation of iron by the chelating agents prevents its incorporation into Pp to form haam by the action of the enzyme ferrochelatase, thereby leading to a build-up of Pp. In this way, the photosensitizing effect is enhanced.

Aminopolycarboxylic acid chelating agents are particularly suitable for use in this regard, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA and well known derivatives/analogues thereof. EDTA is preferred. To achieve the iron-chelating effect, desferrioxamine, and other siderophores may also be used, e.g. in conjunction with aminopolycarboxylic acid chelating agents such as EDTA. The chelating agent may conveniently be used at a concentration of 0.05 to 20% e.g. 0.1 to 10% (w/w).

As described in WO95/07077, it has also been found that surface-penetration assisting agents and especially dialkylsuphoxides such as dimethylsulphoxide (DMSO) may have a beneficial effect in enhancing the photochemotherapeutic effect. Surface-penetration assisting agents for use in the invention may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include HPE-101 (available from Hisamitsu), DMSO and other dialkylsulphoxides, in particular n-decylmethyl-sulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167-177), and Azone® (Stoughton et al., Drug Dpv. Ind. Pharm. 1983, 9: 725-744), or mixtures thereof.

DMSO is however preferred due to its anti-histamine and anti-inflammatory activities and its stimulatory effect on the activity of the enzymes ALA-synthase and ALA-dehydrogenase (the enzymes which, respectively, form and condense ALA to porphobilinogen) thereby enhancing the formation of the active form, Pp.

The surface penetration agent may conveniently be provided in a concentration range of 0.2 to 50% (w/w), e.g. about 10% (w/w).

The compositions of the invention may additionally be formulated and/or administered with other agents, to improve the efficacy of PDT. Furthermore, when treating tumours for example, angiogenesis inhibitors (anti-angiogenic drugs) which have been found to be useful for treating tumours (O'Reilly et al., Nature Medicine, 2, p 689-692, 1996; Yamamoto et al., Anticancer Research, 14, p 1-4, 1994; and Brooks et al., J. Clin. Invest., 96, p 1815-1822, 1995) may be used together with compositions of the invention in PDT to further damage the vascular system of the tumour. Angiogenesis inhibitors which may be used include TNP-470 (AGM-1470, a synthetic analogue of a fungal secretion product called fumagillin; Takeda Chemical Industries Ltd., Osaka, Japan), angiostatin (Surgical Research Lab. at Children's Hospital Medical Center of Harvard Medical School) and integrin $\alpha_v\beta_3$ antagonists (e.g. monoclonal antibody to integrin $\alpha_v\beta_3$, The Scripps Research Institute, LaJolla, Calif.).

Alternatively, or additionally, immunotherapy agents (e.g. antibodies or effectors such as macrophage activating factor) or chemotherapy agents may be used to improve PDT according to the invention. Administration of these supplementary agents should be performed in terms of route, concentration and formulation, according to known methods for using these agents. These additional agents may be administered before, after or during PDT, depending on their function. For example, angiogenesis inhibitors may be added 5 to 10 days after PDT to prevent tumour regrowth.

Other anti-cancer agents may similarly be used in combination with a composition of the invention, either as part of the formulation or as a separate treatment to be administered simultaneously, separately or sequentially.

Glucose has also been found to assist PDT when applied either topically or systemically. When topical administration is contemplated, conveniently the formulation, e.g. a cream, may contain 0.01% to 10% glucose (w/w).

According to the condition being treated, and the nature of the composition, the compounds for use in the invention may be co-administered with such other optional agents, for example in a single composition or they may be administered sequentially or separately. Indeed, in many cases a particularly beneficial photochemotherapeutic effect may be obtained by pre-treatment with the surface-penetration assisting agent in a separate step, prior to administration of the compounds of the invention. Furthermore, in some situations a pre-treatment with the surface-penetration assisting agent, followed by administration of the photochemotherapeutic agent in conjunction with the surface-penetration assisting agent may be beneficial. When a surface-penetration assisting agent is used in pre-treatment this may be used at high concentrations, e.g. up to 100% (w/w). If such a pre-treatment step is employed, the photochemotherapeutic agent may subsequently be administered up to several hours following pre-treatment e.g. at an interval of 5-60 minutes following pre-treatment.

Viewed from a further aspect, the invention thus provides a product comprising an acid addition salt of the invention, together with at least one surface-penetration assisting agent, and optionally one or more chelating agents as a combined preparation for simultaneous, separate or sequential use in treating disorders or abnormalities of external or internal surfaces of the body which are responsive to photochemotherapy.

Alternatively viewed, this aspect of the invention also provides a kit for use in photochemotherapy of disorders or abnormalities of external or internal surfaces of the body comprising:
a) a first container containing an acid addition salt of the invention,
b) a second container containing at least one surface penetration assisting agent; and optionally
c) one or more chelating agents contained either within said first container or in a third container.

It will be appreciated that the method of therapy using compounds as described hereinbefore inevitably involves the provision of intracellular porphyrins which fluoresce at the site of the disorder or abnormality to be treated. Whilst the intensity of this fluorescence may be used to eliminate abnormal cells, the localization of the fluorescence may be used to visualize the size, extent and situation of the abnormality or disorder. Fluorescence may be generated by excitation with blue light (e.g. light in the wavelength region 350-440 nm) and measured in the wavelength region 550-750 nm.

The abnormality or disorder thus identified or confirmed at the site of investigation may then be treated through alternative therapeutic techniques surgical or chemical treatment, or by the method of therapy of the invention by continued build up of fluorescence or through further application of compounds of the invention at the appropriate site. It will be appreciated that diagnostic techniques may require lower levels of fluorescence for visualization than used in therapeutic treatments. Thus, generally, concentration ranges of 0.2 to 30% e.g. 1-5% (w/w) are suitable. Sites, methods and modes of administration have been considered before with regard to the therapeutic uses and are applicable also to diagnostic uses described here.

The compounds of the invention may also be used for in vitro diagnostic techniques, for example for examination of the cells contained in body fluids. The higher fluorescence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention for diagnosis according to the aforementioned methods for photochemotherapy, and products and kits for performing said diagnosis.

A further aspect of the invention relates to a method of in vitro diagnosis, of abnormalities or disorders by assaying a sample of body fluid or tissue of a patient, said method comprising at least the following steps:
i) admixing said body fluid or tissue with an acid addition salt according to the invention,
ii) exposing said mixture to light,
iii) ascertaining the level of fluorescence, and
iv) comparing the level of fluorescence to control levels.

The invention will now be described in more detail in the following non-limiting Examples, with reference to the drawings in which.

EXAMPLE 1

Preparation of hexyl 5-amino-4-oxopentanoate toluenesulfonate

Figure 1:
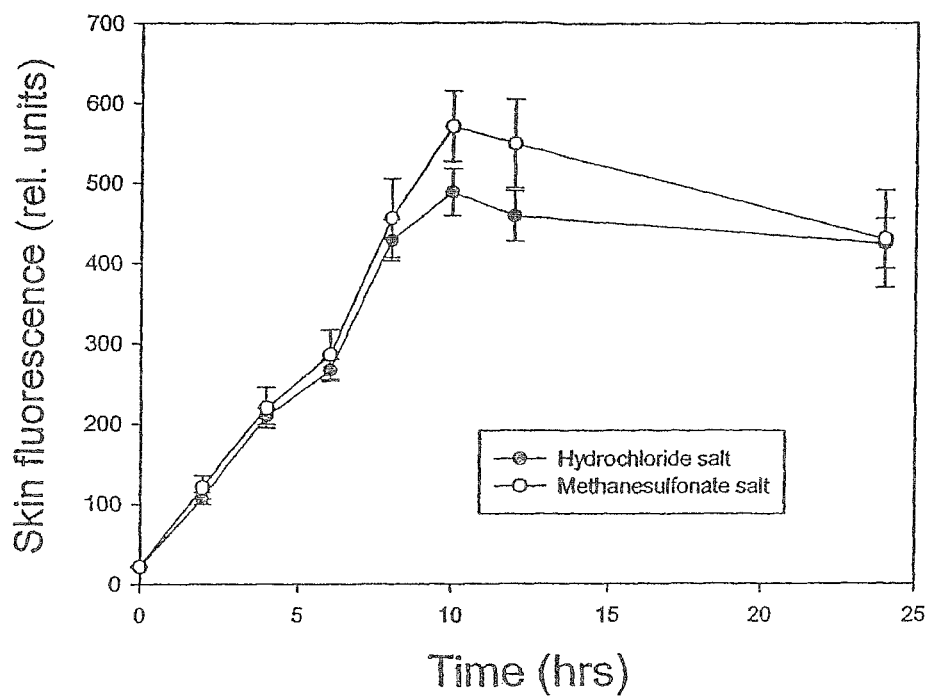
FIG. 1 shows skin fluorescence following topical application of cream formulations containing different salts of 5-amino-4-oxopentanoic acid, bars indicate standard deviation.

Sodium hydrogen carbonate (0.42 g; 5.0 mmol) was added to a solution of hexyl 5-amino-4-oxopentanoate hydrochloride (0.5 g; 2.0 mmol) in water (10 ml) and dichloromethane (5 ml). The mixture was shaken thoroughly and allowed to separate. The organic layer was pipetted off and added to p-toluenesulfonic acid (0.38 g; 2.0 mmol). The aqueous portion was extracted with dichloromethane (1×1 ml). The combined organic solutions were evaporated, leaving a yellow oil that solidified on overnight storage in a freezer. The residue was purified by flash chromatography on a 170×25 mm silica gel 60 column eluted with acetonitrile (150 ml), 5% methanol in acetonitrile (500 ml), and 10% methanol in acetonitrile (250 ml), collecting 15×50 ml fractions. Fractions containing the product were evaporated, leaving 0.31 g (40%) residue.

$^1$H NMR: (200 MHz; DMSO-d$_6$): δ 0.87 (3H, t, J=7 Hz), 1.26 (6H, br s), 1.56 (2H, m), 2.29 (3H, s), 2.54 (2H, t, J=7 Hz), 2.79 (2H, t, J=6 Hz), 4.0 (4H, m), 7.12 (2H, d, J=8 Hz), 7.48 (2H, d, J=8 Hz), 8.04 (3H, br s).

EXAMPLE 2

Preparation of hexyl 5-amino-4-oxopentanoate methanesulfonate (Ion-Exchange Method)

A solution of hexyl 5-amino-4-oxopentanoate hydrochloride (1.0 g; 4.0 mmol) in water (5 ml) and 96% ethanol (5 ml) was passed through a column of Amberlyst A-26(OH) (2.1 g; 8.8 meq) into a solution of methanesulfonic acid (0.38 g; 4.0 mmol) in water (3 ml). The resin column was washed with 50% aq. ethanol (10 ml) and the combined eluents were evaporated to dryness. After drying overnight, the residue was purified by flash chromatography on a 170×25 mm silica gel 60 column eluted with acetonitrile (200 ml), 5 methanol in acetonitrile (500 ml), 7.5% methanol in acetonitrile (500 ml) and 10% methanol in acetonitrile (750 ml), collecting 27×50 ml fractions. Evaporation of fractions containing product gave 0.77 g (62%) residue, mp 132-134° C.

$^1$H NMR: (200 MHz; DMSO-d$_6$): δ 0.87 (3H, t, J=6 Hz), 1.27 (6H, br s), 1.56 (2H, m, J=6 Hz), 2.35 (3H, s), 2.55 (2H, t, J=6 Hz), 2.80 (2H, t, J=6 Hz), 4.00 (4H, m), 8.08 (3H, br s).

$^{13}$C NMR: (50 MHz; DMSO-d$_6$): δ 13.8, 21.8, 24.9, 27.0, 30.8, 34.1, 39.5, 46.6, 64.0, 171.8, 202.4.

EXAMPLE 3

Benzyl 5-amino-4-oxopentanoate methanesulfonate

Prepared from benzyl 5-amino-4-oxopentanoate hydrochloride and methanesulfonic acid using the ion-exchange method, mp 110-115° C.

$^1$H NMR: (200 MHz; DMSO-d$_6$): δ 2.36 (3H, s), 2.63 (2H, t, J=6 Hz), 2.84 (2H, t, J=6 Hz), 3.99 (2H, s), 5.10 (2H, s), 7.37 (5H, m), 8.10 (3H, br s).

$^{13}$C NMR: (50 MHz; DMSO-d$_6$): δ 27.0, 34.1, 39.5, 46.6, 65.5, 127.6, 127.8, 128.2, 135.9, 171.7, 202.4.

EXAMPLE 4

Benzyl 5-amino-4-oxopentanoate toluenesulfonate

Prepared from benzyl 5-amino-4-oxopentanoate hydrochloride and p-toluenesulfonic acid using the ion-exchange method, mp 120-125° C.

$^1$H NMR: (200 MHz; DMSO-d$_6$): δ 2.29 (3H, s), 2.62 (2H, t, J=6 Hz), 2.83 (2H, t, J=6 Hz), 3.99 (2H, s), 5.10 (2H, s), 7.12 (2H, d, J=8 Hz), 7.37 (5H, s), 7.50 (2H, d, J=8 Hz), 8.08 (3H, br s).

$^{13}$C NMR: (50 MHz; DMSO-d$_6$): δ 20.7, 27.0, 34.1, 46.6, 65.5, 127.6, 127.8, 127.9, 128.2, 135.9, 137.6, 145.2, 171.7, 202.4.

EXAMPLE 5

Preparation of 5-amino-4-oxopentanoic acid methanesulfonate (Silver Salt Method)

A solution of 5-amino-4-oxopentanoic acid hydrochloride (1.0 g; 6.0 mmol) in water (5 ml) was added to a stirred solution of silver methanesulfonate (1.22 g; 6.0 mmol) in water (10 ml) in a stoppered erlenmeyer flask wrapped with aluminum foil. The mixture was stirred overnight and transferred to centrifuge tubes. The mixture was centrifuged and decanted. The residue was washed with water (2×1 ml). After centrifuging, the combined aqueous solutions were freeze-dried overnight to give 5-amino-4-oxopentanoic acid methanesulfonate (1.3 g; 96% yield), mp 153.5-154.5° C.

$^1$H NMR: (200 MHz; DMSO-d$_6$): δ 2.39 (3H, s), 2.50 (2H, t, J=6 Hz), 2.72 (2H, t, J=4 Hz), 3.97 (2H, s), 8.08 (3H, br s).

$^{13}$C NMR: (50 MHz; DMSO-d$_6$): δ 27.2, 34.2, 39.5, 46.6, 173.2, 202.6

EXAMPLE 6

5-Amino-4-oxopentanoic acid toluenesulfonate

Prepared from 5-amino-4-oxopentanoic acid hydrochloride and silver p-toluenesulfonate using the silver salt method, mp 185-186° C.

$^1$H NMR: (200 MHz; DMSO-d$_6$): δ 2.29 (3H, s), 2.49 (2H, t, J=6 Hz), 2.74 (2H, t, J=6 Hz), 3.97 (2H, s), 7.12 (2H, d, J=7 Hz), 7.48 (2H, d, J=8 Hz), 8.03 (3H, br s).

$^{13}$C NMR: (50 MHz; DMSO-d$_6$): δ 20.7, 27.1, 34.2, 46.6, 125.2, 127.8, 138, 145, 173.1, 202.6.

EXAMPLE 7

Methyl 5-amino-4-oxopentanoate methanesulfonate

Prepared from methyl 5-amino-4-oxopentanoate hydrochloride and silver methanesulfonate using the silver salt method, mp 135-137° C.

$^1$H NMR: (200 MHz; DMSO-d$_6$): δ 2.29 (3H, s), 2.54 (2H, t, J=8 Hz), 2.79 (2H, t, J=6 Hz), 3.59 3H, s), 3.98 (2H, s), 7.13 (2H, d, J=8 Hz), 7.50 (2H, d, J=8 Hz), 8.07 (3H, br s).

¹³C NMR: (50 MHz; DMSO-d₆): δ 20.7, 26.8, 34.1, 46.6, 51.4, 125.3, 127.9, 137.7, 145.1, 172.2, 202.4.

EXAMPLE 8

Methyl 5-amino-4-oxopentanoate toluenesulfonate

Prepared from methyl 5-amino-4-oxopentanoate hydrochloride and silver p-toluenesulfonate using the silver salt method, mp 138-140° C.
¹H NMR: (200 MHz; DMSO-d₆): δ 2.29 (3H, s), 2.54 (2H, t, J=8 Hz), 2.79 (2H, t, J=6 Hz), 3.59 3H, s), 3.98 (2H, s), 7.13 (2H, d, J=8 Hz), 7.50 (2H, d, J=8 Hz), 8.07 (3H, br s).
¹³C NMR: (50 MHz; DMSO-d₆): δ 20.7, 26.8, 34.1, 46.6, 51.4, 125.3, 127.9, 137.7, 145.1, 172.2, 202.4.

EXAMPLE 9

Hexyl 5-amino-4-oxopentanoate methanesulfonate

Prepared from hexyl 5-amino-4-oxopentanoate hydrochloride and silver methanesulfonate using the silver salt method, mp 125° C. and 134-136° C. (different crystalline forms).
¹H NMR: (200 MHz; DMSO-d₆): δ 0.87 (3H, t, J=6 Hz), 1.27 (6H, br s), 1.56 (2H, m, J=6 Hz), 2.35 (3H, s), 2.55 (2H, t, J=6 Hz), 2.80 (2H, t, J=6 Hz), 4.00 (4H, m), 8.08 (3H, br s).
¹³C NMR: (50 MHz; DMSO-d₆): δ 13.8, 21.8, 24.9, 27.0, 30.8, 34.1, 39.5, 46.6, 64.0, 171.8, 202.4.

EXAMPLE 10

Hexyl 5-amino-4-oxopentanoate toluenesulfonate

Prepared from hexyl 5-amino-4-oxopentanoate hydrochloride and silver p-toluenesulfonate using the silver salt method, mp 116-118° C.
¹H NMR: (200 MHz; DMSO-d₆): δ 0.86 (3H, t, J=6 Hz), 1.26 (6H, br s), 1.53 (2H, m), 2.29 (3H, s), 2.53 (2H, t, J=6 Hz), 2.78 (2H, t, J=6 Hz), 4.0 (4H, m), 7.12 (2H, d, J=8 Hz), 7.50 (2H, d, J=8 Hz), 8.06 (3H, br s).
¹³C NMR: (50 MHz; DMSO-d₆): δ 13.8, 20.7, 21.9, 24.9, 27.0, 28.0, 30.8, 34.1, 46.6, 64.0, 125.3, 127.9, 137.6, 145.2, 171.8, 202.4.

EXAMPLE 11

2-Methyl-1-pentyl 5-amino-4-oxopentanoate methanesulfonate

Prepared from 2-methyl-1-pentyl 5-amino-4-oxopentanoate hydrochloride and silver methanesulfonate using the silver salt method, mp 128-133° C.
¹H NMR: (200 MHz; DMSO-d₆): δ 0.88 (6H, m), 1.0-1.4 (4H, m), 1.74 (1H, m, J=6 Hz), 2.35 (3H, s), 2.56 (2H, t, J=6 Hz), 2.81 (2H, t, J=8 Hz), 3.75-3.96 (2H, m), 3.97 (2H, s), 8.12 (3H, br s).
¹³C NMR: (50 MHz; DMSO-d₆): δ 14.0, 16.5, 19.3, 23.6, 27.0, 31.6, 34.1, 34.9, 39.5, 46.6, 68.6, 171.8, 202.4.

EXAMPLE 12

2-Methyl-1-pentyl 5-amino-4-oxopentanoate toluenesulfonate

Prepared from 2-methyl-1-pentyl 5-amino-4-oxopentanoate hydrochloride and silver p-toluenesulfonate using the silver salt method, mp 125-127° C.
¹H NMR: (200 MHz; DMSO-d₆): δ 0.88 (6H, t, J=6 Hz), 1.0-1.4 (4H, m), 1.73 (1H, m), 2.29 (3H, s), 2.56 (2H, t, J=6 Hz), 2.80 (2H, t, J=6 Hz), 3.75-4.0 (2H, m), 3.98 (2H, s), 7.12 (2H, d, J=8 Hz), 7.49 (2H, d, J=8 Hz), 8.03 (3H, br s).
¹³C NMR: (50 MHz; DMSO-d₆): δ 14.0, 16.5, 19.3, 20.7, 23.6, 26.9, 31.6, 34.1, 34.8, 46.6, 68.6, 125.3, 127.8, 137.4, 145.2, 171.8, 202.4.

EXAMPLE 13

4-Methyl-1-pentyl 5-amino-4-oxopentanoate methanesulfonate

Prepared from 4-methyl-1-pentyl 5-amino-4-oxopentanoate hydrochloride and silver methanesulfonate using the silver salt method, mp 75-85° C. and 110-115° C. (different crystalline forms).
¹H NMR: (200 MHz; DMSO-d₆): δ 0.86 (6H, d, J=6 Hz), 1.20 (2H, m), 1.53 (2H, m, 2.39 (3H, s), 2.55 (2H, t, J=6 Hz), 2.80 (2H, t, J=8 Hz), 3.90-4.04 (4H, m), 8.18 (3H, br s).
¹³C NMR: (50 MHz; DMSO-d₆): δ 22.3, 25.9, 27.0, 27.0, 34.1, 34.3, 39.5, 46.6, 64.2, 171.8, 202.4.

EXAMPLE 14

4-Methyl-1-pentyl 5-amino-4-oxopentanoate toluenesulfonate

Prepared from 4-methyl-1-pentyl 5-amino-4-oxopentanoate hydrochloride and silver p-toluenesulfonate using the silver salt method, mp 96-100° C.
¹H NMR: (200 MHz; DMSO-d₆): δ 0.86 (6H, t, J=6 Hz), 1.16 (2H, m), 1.53 (1H, m), 2.29 (3H, s), 2.57 (2H, t, J=6 Hz), 2.78 (2H, t, J=6 Hz), 3.95-4.05 (4H, m), 7.13 (2H, d, J=8 Hz), 7.51 (2H, d, J=8 Hz), 8.06 (3H, br s).
¹³C NMR: (50 MHz; DMSO-d₆): δ 20.7, 22.3, 25.9, 27.0, 27.0, 34.1, 34.3, 46.6, 64.2, 125.3, 127.9, 137.6, 145.1, 171.8, 202.4.

EXAMPLE 15

2-(2-Ethoxyethoxy)ethyl 5-amino-4-oxopentanoate benzenesulfonate

Prepared from 2-(2-ethoxyethoxy)ethyl 5-amino-4-oxopentanoate hydrochloride and silver benzenesulfonate using the silver salt method, mp 52-56° C.
¹H NMR: (200 MHz; DMSO-d₆): δ 1.10 (3H, t, J=7 Hz), 2.57 (2H, t, J=6 Hz), 2.79 (2H, t, J=6 Hz), 3.35-3.65 (8H, m), 3.98 (2H, s), 4.12 (2H, t, J=5 Hz), 7.25-7.36 (3H, m), 7.55-7.65 (2H, m), 8.04 (3H, br s).
¹³C NMR: (50 MHz; DMSO-d₆): δ 15.0, 27.0, 34.1, 46.6, 63.4, 65.5, 68.0, 69.0, 69.7, 125.3, 127.4, 128.3, 147.8, 171.8, 202.4.

EXAMPLE 16

Benzyl 5-amino-4-oxopentanoate methanesulfonate

Prepared from benzyl 5-amino-4-oxopentanoate hydrochloride and silver methanesulfonate using the silver salt method, mp 132-135° C.
¹H NMR: (200 MHz; DMSO-d₆): δ 2.36 (3H, s), 2.63 (2H, t, J=6 Hz), 2.84 (2H, t, J=6 Hz), 3.99 (2H, s), 5.10 (2H, s), 7.37 (5H, m), 8.10 (3H, br s).

$^{13}$C NMR: (50 MHz; DMSO-d$_6$): δ 27.0, 34.1, 39.5, 46.6, 65.5, 127.6, 127.8, 128.2, 135.9, 171.7, 202.4.

EXAMPLE 17

Benzyl 5-amino-4-oxopentanoate 2-hydroxyethanesulfonate

Prepared from benzyl 5-amino-4-oxopentanoate hydrochloride and silver 2-hydroxyethanesulfonate using the silver salt method, mp 76-82° C.

$^1$H NMR: (200 MHz; DMSO-d$_6$): δ 2.63 (2H, t, J=6 Hz), 2.67 (2H, t, J=6 Hz), 2.84 (2H, t, J=6 Hz), 3.65 (2H, t, J=7 Hz), 3.98 (2H, s), 5.10 (2H, s), 7.37 (5H, m), 8.13 (3H, br s).

$^{13}$C NMR: (50 MHz; DMSO-d$_6$): δ 27.0, 34.1, 46.6, 53.5, 57.5, 65.5, 127.6, 127.8, 128.2, 135.9, 171.7, 202.4.

EXAMPLE 18

Benzyl 5-amino-4-oxopentanoate (1S)-10-camphorsulfonate

Prepared from benzyl 5-amino-4-oxopentanoate hydrochloride and silver (1S)-10-camphorsulfonate using the silver salt method, viscous oil.

$^1$H NMR: (200 MHz; DMSO-d$_6$): δ 0.75 (3H, s), 1.04 (3H, s), 1.31 (2H, m), 1.75-1.97 (3H, m), 2.24 (1H, dt, J=4 and 18 Hz), 2.40 (1H, d, J=16 Hz), 2.63 (2H, t, J=6 Hz), 2.84 (2H, t, J=6 Hz), 2.90 (1H, d, J=16 Hz), 3.99 (2H, s), 5.10 (2H, s), 7.36 (5H, s), 8.08 (3H, br s).

$^{13}$C NMR: (50 MHz; DMSO-d$_6$): δ 19.4, 20.0, 24.0, 26.3, 27.0, 42.0, 42.1, 42.1, 46.5, 46.6, 46.9, 58.1, 65.5, 127.6, 127.8, 128.2, 135.9, 171.7, 202.4, 216.0.

EXAMPLE 19

Benzyl 5-amino-4-oxopentanoate benzenesulfonate

Prepared from benzyl 5-amino-4-oxopentanoate hydrochloride and silver benzenesulfonate using the silver salt method, mp 100-103° C.

$^1$H NMR: (200 MHz; DMSO-d$_6$): δ 2.62 (2H, t, J=6 Hz), 2.83 (2H, t, J=6 Hz), 3.99 (2H, s), 5.10 (2H, s), 7.30-7.40, 7.60-7.70 (10H, m), 8.08 (3H, br s).

$^{13}$C NMR: (50 MHz; DMSO-d$_6$): δ 27.0, 34.1, 46.6, 65.5, 122.9, 125.3, 127.5, 127.6, 127.8, 128.2, 128.2, 135.9, 147.8, 171.7, 202.4.

EXAMPLE 20

Benzyl 5-amino-4-oxopentanoate toluenesulfonate

Prepared from benzyl 5-amino-4-oxopentanoate hydrochloride and silver p-toluenesulfonate using the silver salt method, mp 146-148° C.

$^1$H NMR: (200 MHz; DMSO-d$_6$): δ 2.29 (3H, s), 2.62 (2H, t, J=6 Hz), 2.83 (2H, t, J=6 Hz), 3.99 (2H, s), 5.10 (2H, s), 7.12 (2H, d, J=8 Hz), 7.37 (5H, s), 7.50 (2H, d, J=8 Hz), 8.08 (3H, br s).

$^{13}$C NMR: (50 MHz; DMSO-d$_6$): δ 20.7, 27.0, 34.1, 46.6, 65.5, 127.6, 127.8, 127.9, 128.2, 135.9, 137.6, 145.2, 171.7, 202.4.

EXAMPLE 21

Benzyl 5-amino-4-oxopentanoate 2-naphthalenesulfonate

Prepared from benzyl 5-amino-4-oxopentanoate hydrochloride and silver 2-naphthalenesulfonate using the silver salt method, mp 137-141° C. (dec.).

$^1$H NMR: (200 MHz; DMSO-d$_6$): δ 2.62 (2H, t, J=6 Hz), 2.84 (2H, t, J=6 Hz), 4.00 (2H, s), 5.10 (2H, s), 7.12 (2H, d, J=8 Hz), 7.36 (5H, s), 7.49 (2H, m), 7.74 (1H, dd, J=2 and 8 Hz), 7.86-8.00 (4H, m), 8.18 (3H, br s).

$^{13}$C NMR: (50 MHz; DMSO-d$_6$): δ 27.0, 34.1, 46.6, 65.5, 123.7, 123.9, 126.1, 126.3, 127.2, 127.6, 127.8, 128.2, 131.9, 132.6, 134.7, 135.9, 137.6, 145.1, 171.7, 202.4.

EXAMPLE 22

4-Methylbenzyl 5-amino-4-oxopentanoate methanesulfonate

Prepared from 4-methylbenzyl 5-amino-4-oxopentanoate hydrochloride and silver methanesulfonate using the silver salt method, mp 120-124° C.

$^1$H NMR: (200 MHz; DMSO-d$_6$): δ 2.30 (3H, s), 2.36 (3H, s), 2.61 (2H, t, J=6 Hz), 2.83 (3H, m), 3.98 (2H, s), 5.05 (2H, s), 7.22 (4H, m), 8.14 (3H, br s).

$^{13}$C NMR: (50 MHz; DMSO-d$_6$): δ 20.6, 23.6, 27.0, 34.1, 39.5, 46.6, 65.4, 127.8, 128.8, 132.8, 137.1, 171.7, 202.4.

EXAMPLE 23

4-Methylbenzyl 5-amino-4-oxopentanoate toluenesulfonate

Prepared from 4-methylbenzyl 5-amino-4-oxopentanoate hydrochloride and silver p-toluenesulfonate using the silver salt method, mp 115-119° C.

$^1$H NMR: (200 MHz; DMSO-d$_6$): δ 2.29 (3H, s), 2.30 (3H, s), 2.59 (2H, t, J=6 Hz), 2.82 (3H, m), 3.97 (2H, s), 5.04 (2H, s), 7.19 (6H, m, J=8 Hz), 7.50 (2H, d, J=8 Hz), 8.18 (3H, br s).

$^{13}$C NMR: (50 MHz; DMSO-d$_6$): δ 20.7, 27.0, 34.1, 46.5, 65.4, 125.3, 127.8, 127.9, 128.8, 132.8, 137.1, 137.6, 145.2, 171.7, 202.4

EXAMPLE 24

4-Isopropylbenzyl 5-amino-4-oxopentanoate methanesulfonate

Prepared from 4-isopropylbenzyl 5-amino-4-oxopentanoate hydrochloride and silver methanesulfonate using the silver salt method, mp 113-115° C. and 125-127° C. (different crystalline forms).

$^1$H NMR: (200 MHz; DMSO-d$_6$): δ 1.20 (6H, d, J=6 Hz), 2.36 (3H, s), 2.62 (2H, t, J=6 Hz), 2.85 (3H, m), 3.99 (2H, s), 5.06 (2H, s), 7.27 (4H, m), 8.15 (3H, br s).

$^{13}$C NMR: (50 MHz; DMSO-d$_6$): δ 23.7, 27.0, 33.1, 34.1, 39.5, 46.6, 65.4, 126.1, 127.9, 133.2, 148.1, 171.7, 202.4.

EXAMPLE 25

4-Isopropylbenzyl 5-amino-4-oxopentanoate toluenesulfonate

Prepared from 4-isopropylbenzyl 5-amino-4-oxopentanoate hydrochloride and silver p-toluenesulfonate using the silver salt method, mp 121-123° C.

$^1$H NMR: (200 MHz; DMSO-d): δ 1.20 (6H, d, J=6 Hz), 2.29 (3H, s), 2.60 (2H, t, J=6 Hz), 2.82 (2H, t, J=6 Hz), 2.88 (1H, m), 3.98 (2H, s), 5.05 (2H, s), 7.12 (2H, d, J=8 Hz), 7.26 (4H, d, J=2 Hz), 7.50 (2H, d, J=8 Hz), 8.10 (3H, br s).

$^{13}$C NMR: (50 MHz; DMSO-d$_6$): δ 20.7, 2.7, 27.0, 33.1, 34.1, 46.6, 65.4, 125.3, 126.1, 127.8, 133.2, 137.5, 145.5, 148.1, 171.7, 202.4.

EXAMPLE 26

5-amino-4-oxopentanoic acid hydrobromide

A stirred mixture of methyl 5-phthalimido-4-oxopentanoate (4.0 g, 14.5 mmol) [Z. Naturforsch. 41B, 1593-94 (1986)] and 48% hydrobromic acid (40 ml) was refluxed for 7 hrs, then cooled to room temperature and stored overnight in a refrigerator. Following filtering the residue was washed with water and the combined filtrates were evaporated to dryness on a rotary evaporator and titrated with diethyl ether (2×25 ml). The residue was filtered and dried over silica gel at 30° C. and 15 mm Hg in a drying pistol. The crude product was dissolved in methanol (10 ml) and 2-propanol (30 ml). Diethyl ether (150 ml) was added and the mixture was allowed to stand 2 hrs. The precipitate was filtered and dried as before, to give 2.5 g (81%), mp 137-140° C.

$^1$H NMR: (200 MHz; DMSO-d$_6$): δ 2.49 (2H, t, J=6 Hz), 2.76 (2H, t, J=6 Hz), 3.99 (2H, s), 8.13 (3H, br s).

$^{13}$C NMR: (50 MHz; DMSO-d$_6$): δ 27.1, 34.3, 46.6, 173.1, 202.5.

EXAMPLE 27

Benzyl 5-amino-4-oxopentanoate hydrobromide

A stirred mixture of 5-amino-4-oxopentanoic acid hydrobromide (1.60 g, 7.5 mmol), benzyl alcohol (15 ml), and 48% hydrobromic acid (8 drops) was heated to 80° C. (bath temperature) for 2 days. The mixture was cooled to room temperature and excess benzyl alcohol was removed with a rotary evaporator at 0.12 mm Hg. The residue was titrated with diethyl ether (2×50 ml) and the residue was purified by flash chromatography on a 160×55 mm silica gel 60 column eluted sequentially with acetonitrile, 5% methanol in acetonitrile, and 10% methanol in acetonitrile. Fractions containing the product were combined and evaporated. The residue was titrated with diethyl ether (5×15 ml), filtered, and dried at 30° C. and 15 mm Hg to give 0.97 g (43%) tan powder, mp 62-67° C.

$^1$H NMR: (200 MHz; DMSO-d$_6$): δ 2.63 (2H, t, J=6 Hz), 2.86 (2H, t, J=6 Hz), 4.02 (2H, s), 5.10 (2H, s), 7.37 (5H, s), 8.16 (3H, br s).

$^{13}$C NMR: (50 MHz; DMSO-d$_6$): δ 27.0, 34.2, 39.5, 46.5, 65.5, 127.6, 127.8, 128.2, 135.9, 171.7, 202.3.

EXAMPLE 28

Benzyl 5-amino-4-oxopentanoate nitrate

Prepared from benzyl 5-amino-4-oxopentanoate hydrochloride and silver nitrate using the silver salt method, mp 82-86° C.

$^1$H NMR: (200 MHz; DMSO-d$_6$): δ 2.63 (2H, t, J=6 Hz), 2.84 (2H, t, J=6 Hz), 4.00 (2H, s), 5.10 (2H, s), 7.37 (5H, s), 8.10 (3H, br s).

$^{13}$C NMR: (50 MHz; DMSO-d$_6$): δ 27.0, 34.1, 39.5, 46.6, 65.5, 127.6, 127.8, 128.2, 135.9, 171.7, 202.4.

EXAMPLE 29

Benzyl 5-amino-4-oxopentanoate sulfate (2:1)

Prepared from benzyl 5-amino-4-oxopentanoate hydrochloride (0.52 g; 2.0 mmol) and Ag$_2$SO$_4$ (0.31 g; 1.0 mmol) in water (10 mL) using the silver salt method. Yield after drying over silica gel was 0.51 g (94%). Mp 106-109° C.

Elemental analysis (carried out by Ilse Beetz Mikroanalytisches Laboratorium, 96301 Kronach, Germany):

| % C | calc. | 53.32% | found | 53.37% |
| % H | calc. | 5.97% | found | 5.97% |
| % S | calc. | 5.93% | found | 5.78% |

The elemental analysis shows that the product exists as the sulfate (2:1), i.e. (benzyl 5-amino-4-oxopentanoate)

EXAMPLE 30

Benzyl 5-amino-4-oxopentanoate phosphate

Prepared from benzyl 5-amino-4-oxopentanoate hydrochloride (0.52 g; 2.0 mmol) and Ag$_3$PO$_4$ (0.28 g; 0.67 mmol) in water (10 mL) using the silver salt method. Yield after drying over silica gel was 0.36 g. Mp 93-95° C.

Elemental analysis (carried out by Ilse Beetz Mikroanalytisches Laboratorium, 96301 Kronach, Germany):

|  | $PO_4^{3-}$ | $HPO_4^{2-}$ |  |
| --- | --- | --- | --- |
| % C | calc. 56.76% | calc. 53.33% | found 53.62% |
| % H | calc. 6.35% | calc. 6.15% | found 6.08% |
| % P | calc. 4.07% | calc. 5.73% | found 3.90% |

The elemental analysis indicates that the product is not the expected phosphate (3:1); the closest match for C and H is the monohydrogen phosphate (benzyl 5-amino-4-oxopentanoate. The comparatively low value for P could be caused by incomplete reaction, e.g. some chloride may still be present.

EXAMPLE 31

Formulations

Different salts of 5-amino-4-oxopentanoic acid or of its esters were formulated in Unguentum Merck for dermal studies. All cream formulations contained 0.5 mmol of substance per 10 g cream to ensure the same molar concentration (assuming that 10 g cream equals 10 ml, the approx. molar concentration is 0.5 mmol/10 ml or 50 mM). Preparation of the formulations is outlined in Table 1 below.

TABLE 1

Dermal formulations

| Substance-salt* | Mol. wt. | Formulation** (mg/10 g cream) |
| --- | --- | --- |
| 5-amino-4-oxopentanoic acid-HCl | 168 | 85 |
| 5-amino-4-oxopentanoic acid-methanesulfonate | 211 | 105 |

TABLE 1-continued

Dermal formulations

| Substance-salt* | Mol. wt. | Formulation** (mg/10 g cream) |
|---|---|---|
| hexyl 5-amino-4-oxopentanoate-HCl | 251 | 125 |
| hexyl 5-amino-4-oxopentanoate-methanesulfonate | 294 | 150 |
| hexyl 5-amino-4-oxopentanoate-toluenesulfonate | 372 | 190 |
| methyl 5-amino-4-oxopentanoate-HCl | 181 | 100 |
| methyl 5-amino-4-oxopentanoate-methanesulfonate | 224 | 125 |
| methyl 5-amino-4-oxopentanoate-toluenesulfonate | 302 | 170 |
| benzyl 5-amino-4-oxopentanoate-HCl | 258 | 130 |
| benzyl 5-amino-4-oxopentanoate-methanesulfonate | 301 | 150 |
| benzyl 5-amino-4-oxopentanoate-toluenesulfonate (a) | 379 | 190 |

*All salts were prepared by the silver salt method except for the substance marked with (a) which was prepared by the ion exchange method.
**All formulations contained 0.5 mmol salt per 10 g cream

EXAMPLE 32

Biological Activity—Salts of 5-amino-4-oxopentanoic acid

Method: Female Balb/c athymic nude mice, weighing about 22 g, obtained from the Department of Laboratory Animals, The Norwegian Radium Hospital, Oslo, Norway, were used in the study. Each group consisted of three mice.

Each mouse received 0.05-0.1 g of formulation (see Example 31) topically applied at the right flank of the body, evenly distributed and covered with a dressing (Opsite Flexigrid; Smith and Nephew Medical Ltd., Hull, England).

The fiber point measuring device used consisted of a bundle of optical fibers connected to a spectrofluorimeter which produced the excitation light of 407 nm. The excitation light, which is capable of penetrating 0.1-0.5 mm into the tissue, was led through half of the fibers to the mouse skin. The resulting emission fluorescence spectrum (550-750) nm was collected and led through the remaining fibers into a photomultiplier for quantification. The fluorescence spectrum from the skin was measured at 0, 2, 4, 6, 8, 10, 12 and 24 hours after administration and plotted against time.

Results: It can be seen from FIG. 1 that the methanesulfonate salt gave somewhat higher maximal skin fluorescence than the HCl salt.

EXAMPLE 33

Biological Activity—Salts of benzyl 5-amino-4-oxopentanoate

Preparation of formulations is described in Example 31. The same experimental system as in Example 32 was used, and the results are shown in FIG. 2.

Figure 2:
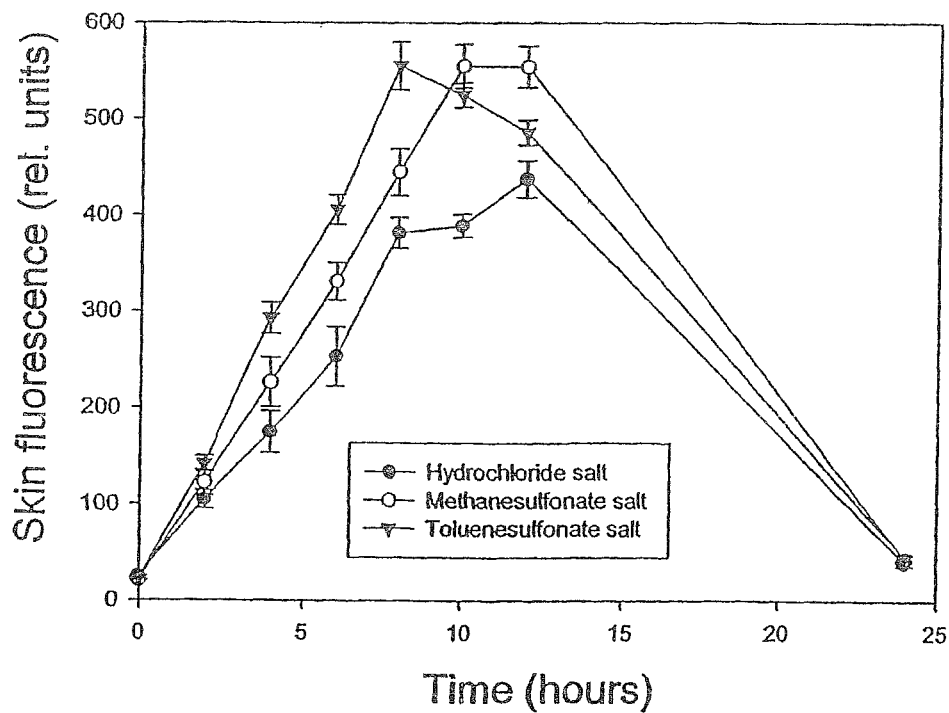
FIG. 2 shows skin fluorescence following topical application of cream formulations containing hydrochloride, tosylate and mesylate salts of benzyl 5-amino-4-oxopentanoate, bars indicate standard deviation.

It can be seen from FIG. 2 that both the methanesulfonate and the toluenesulfonate salts gave 25-30% higher maximal fluorescence than the hydrochloride salt. Both the initial fluorescence build-up occurred faster and the maximum fluorescence occurred faster for the methanesulfonate and the toluenesulfonate salts than for the hydrochloride salt.

EXAMPLE 34

Biological Activity—Salts of methyl 5-amino-4-oxopentanoate

Preparation of formulations is described in Example 31. The same experimental system as in Example 32 was used, and the results are shown in FIG. 3.

Figure 3:
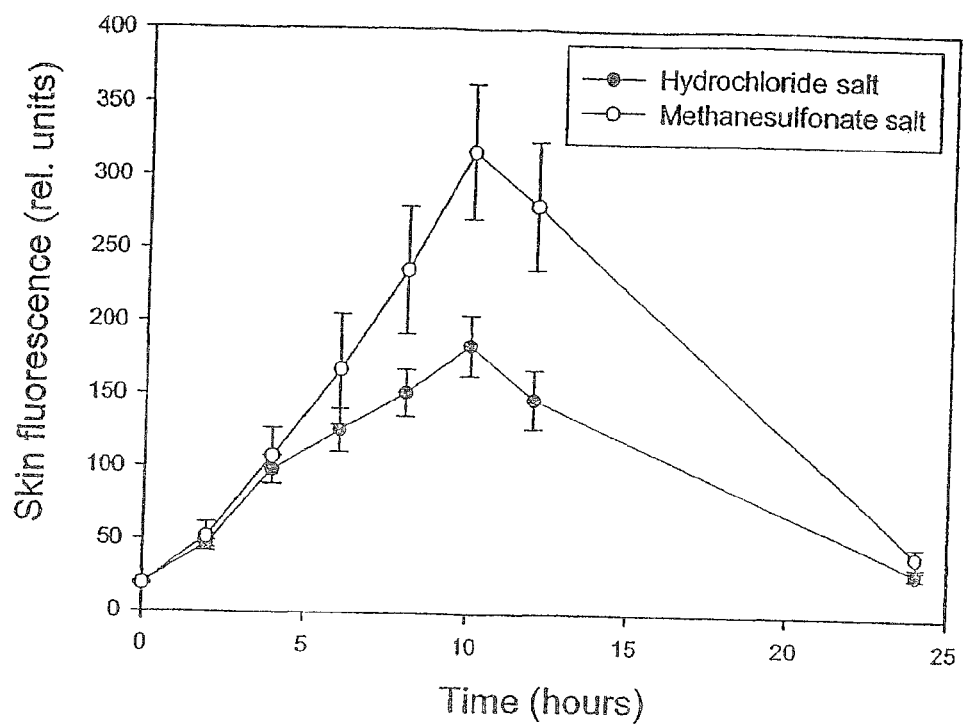
FIG. 3 shows skin fluorescence following topical application of cream formulations containing hydrochloride and methanesulfonate salts of methyl 5-amino-4-oxopentanoate, bars indicate standard deviation.

It can be seen from FIG. 3 that the methanesulfonate-salt of methyl 5-aminolevulinate gave a considerable increase in skin fluorescence as compared to the hydrochloride salt.

EXAMPLE 35

Biological Activity—Salts of hexyl 5-amino-4-oxopentanoate

Preparation of formulations is described in Example 31. The same experimental system as in Example 32 was used, and the results are shown in FIG. 4.

Figure 4:
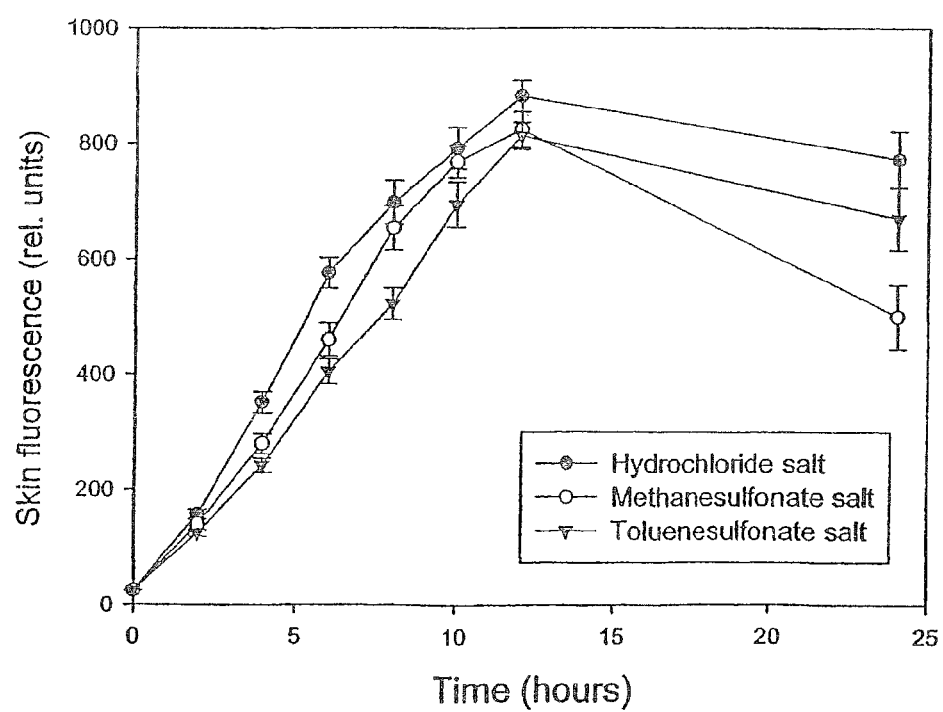
FIG. 4 shows skin fluorescence following topical application of cream formulations containing hydrochloride, methanesulfonate and toluenesulfonate salts of methyl 5-amino-4-oxopentanoate, bars indicate standard deviation.

It can be seen from FIG. 4 that the methanesulfonate- and toluenesulfonate salts of hexyl 5-aminolevulinate gave approx. the same skin fluorescence as the hydrochloride salt.

EXAMPLE 36

Formulations

Different salts of 5-amino-4-oxopentanoic acid or of its benzylester were formulated in Unguentum Merck for dermal studies. All cream formulations contained 0.5 mmol substance per 10 g cream to assure the same molar concentration. Corrections were made in the case of the 2:1 salts so that the molar concentration of 5-amino-4-oxopentanoic acid or the corresponding ester corresponded to 0.5 mmol/10 g cream. Assuming that 10 g cream equals 10 ml, the approx. molar concentration is 0.5 mmol/10 ml=50 mM. Preparation of the formulations is outlined in Table 2 below.

TABLE 2

Dermal formulations

| Substance-salt | Mol. wt | Formulation (mg/10 g cream) |
|---|---|---|
| 5-amino-4-oxopentanoic acid-HCl | 168 | 85 |
| 5-amino-4-oxopentanoic acid-HBr | 213 | 107 |
| benzyl 5-amino-4-oxopentanoate-HCl | 258 | 130 |
| benzyl 5-amino-4-oxopentanoate-HBr | 302 | 151 |
| benzyl 5-amino-4-oxopentanoate-HNO$_3$ | 284 | 142 |
| benzyl 5-amino-4-oxopentanoate-benzenesulfonate | 378 | 189 |
| benzyl 5-amino-4-oxopentanoate-sulphate | 269* | 135 |
| benzyl 5-amino-4-oxopentanoate-phosphate | 261* | 131 |

*Assuming ½ mole of sulphate or hydrogenphosphate per mole of benzyl 5-amino-4-oxopentanoate.

EXAMPLE 37

Biological Activity—Salts of 5-amino-4-oxopentanoic acid

Figure 5:
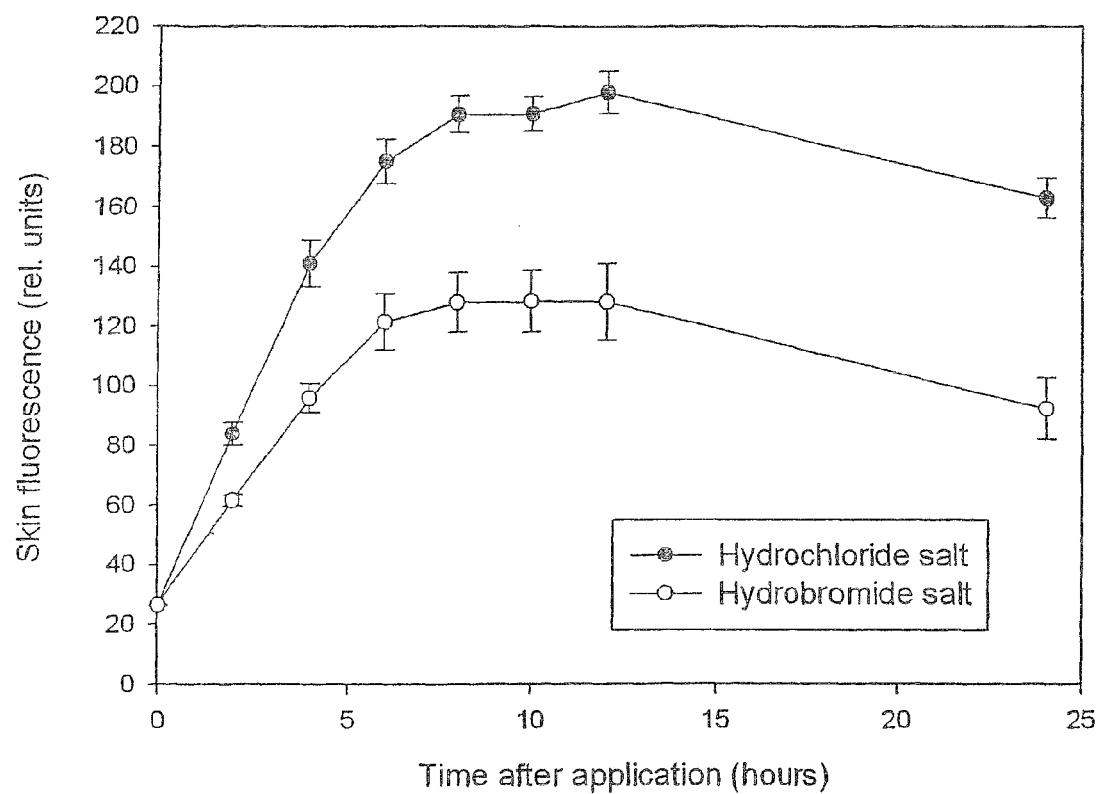
FIG. 5 shows skin fluorescence following topical application of cream formulations containing hydrochloride and hydrobromide salts of 5-amino-4-oxopentanoic acid, bars indicate standard deviation.

Preparation of the Formulations is Described in Example 36. The same experimental system as in Example 32 was used, except that the skin fluorescence was measured at 636 nm rather than at 550-750 nm. The results are shown in FIG. 5.

EXAMPLE 38

Biological Activity—Salts of benzyl 5-amino-4-oxopentanoate

Preparation of the Formulations is Described in Example 36. The same experimental system as in Example 37 was used. The results are shown in FIGS. 6 and 7.

Figure 6:
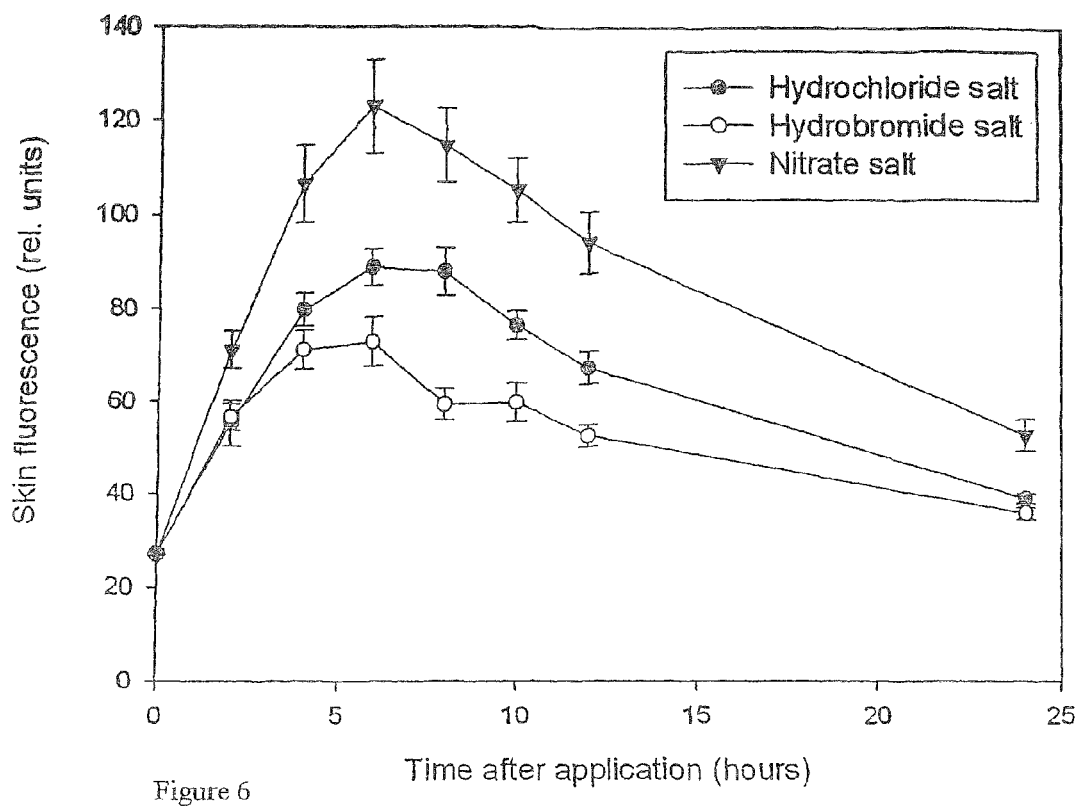
FIG. 6 shows skin fluorescence following topical application of cream formulations containing hydrochloride, hydrobromide and nitrate salts of benzyl 5-amino-4-oxopentanoic acid, bars indicate standard deviation.

It can be seen from FIG. 6 that the nitrate salt of benzyl 5-amino-4-oxopentanoate was more effective in inducing skin fluorescence than the hydrochloride salt.

Figure 7:
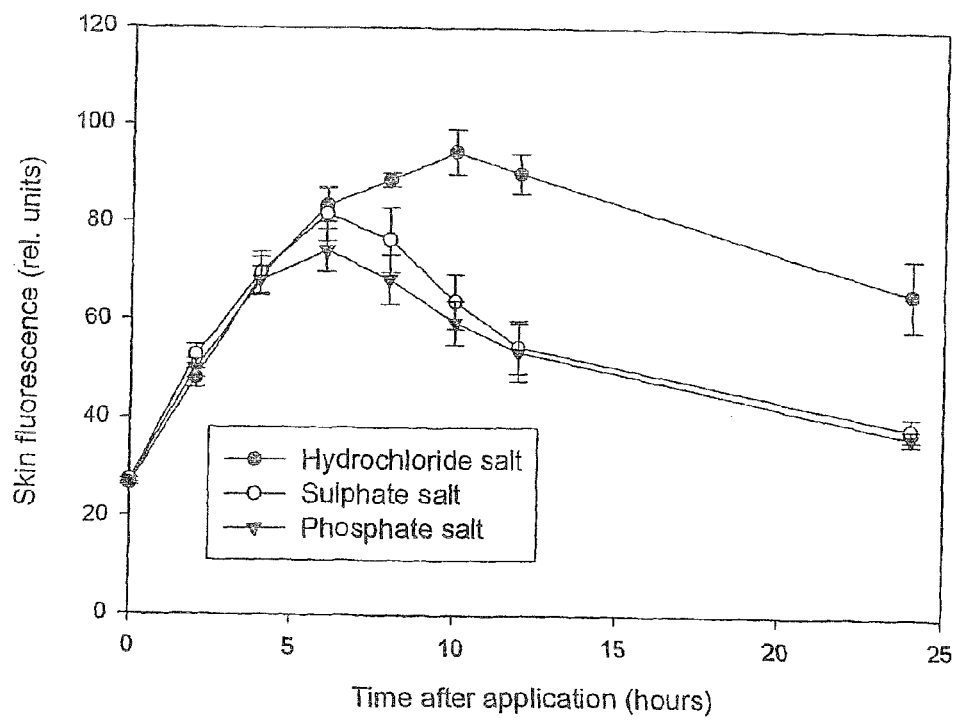
FIG. 7 shows skin fluorescence following topical application of cream formulations containing hydrochloride, sulphate and phosphate salts of benzyl 5-amino-4-oxopentanoic acid, bars indicate standard deviation.

It can be seen from FIG. 7 that the sulphate- and phosphate-salts of benzyl 5-amino-4-oxopentanoate were poorer inducers of skin fluorescence than the corresponding hydrochloride salt. However, the maximum fluorescence occurred earlier for the sulphate- and phosphate-salts than for the hydrochloride salt.

EXAMPLE 39

Hygroscopicity of hexyl 5-amino-4-oxopentanoate hydrochloride, methanesulfonate, and toluenesulfonate Samples (2 mg) of the hydrochloride, methanesulfonate, and toluenesulfonate of hexyl 5-amino-4-oxopentanoate were kept at ambient temperature and ambient humidity for 4 days. No observable change.

Samples (2 mg) of the hydrochloride, methanesulfonate, and toluenesulfonate of hexyl 5-amino-4-oxopentanoate were kept at ambient temperature and 100 humidity. The hydrochloride had deliquesced after standing overnight. The methanesulfonate had deliquesced after two days, while the toluenesulfonate had deliquesced after four days.

EXAMPLE 40

Hygroscopicity of methyl 5-amino-4-oxopentanoate hydrochloride, methanesulfonate, and toluenesulfonate Samples of methyl 5-amino-4-oxopentanoate hydrochloride, methanesulfonate, and toluenesulfonate were weighed and kept in 30 ml plastic cups in a closed chamber at 75-84% relative humidity over saturated ammonium sulfate solution at ambient temperature (ca. 25° C.). The samples were then weighed after different intervals of time to monitor water uptake. The appearance of the samples was also checked at the same time to determine the onset of deliquescence. The results are shown in FIG. 8.

Figure 8:
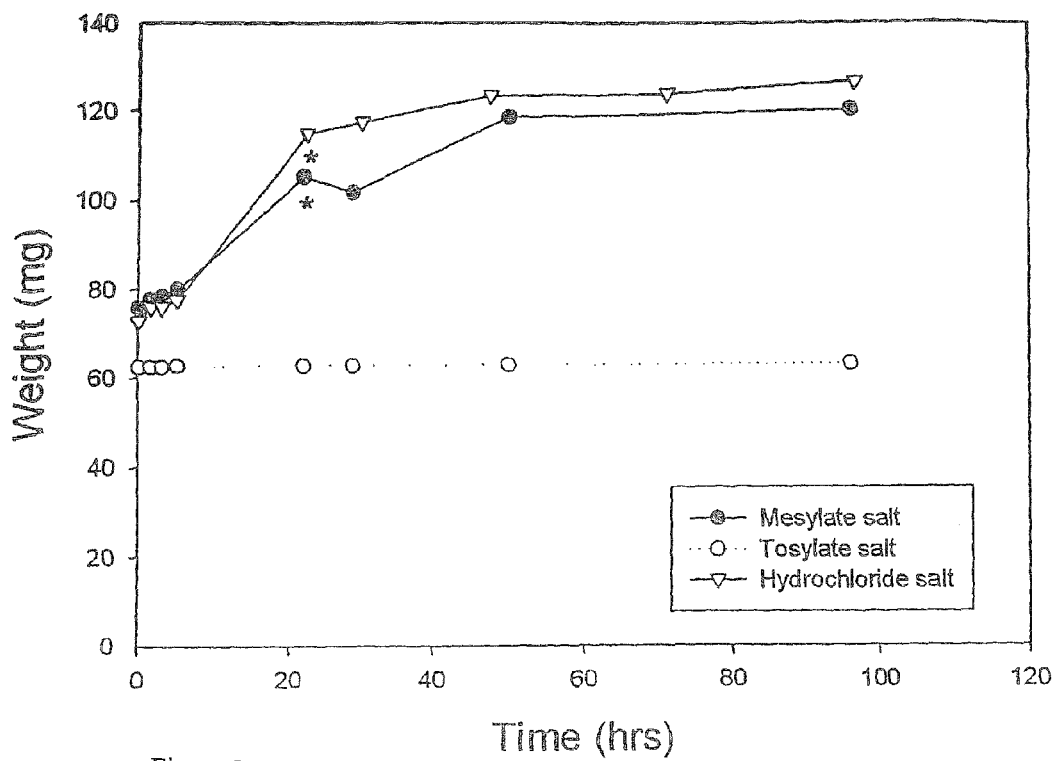
FIG. 8 shows the hygroscopicity of hydrochloride, methanesulfonate and toluenesulfonate salts of methyl 5-amino-4-oxopentanoic acid.

It can be seen from FIG. 8 that both the hydrochloride and mesylate salts took up water to a considerable extent as monitored by weight and that the onset of deliquescence occurred after 22 hrs (as indicated by asterisks in the figure). In contrast, the tosylate salt of methyl 5-amino-4-oxopentanoate did not pick up water and did not change appearance during the test period.

EXAMPLE 41

Hygroscopicity of 5-amino-4-oxopentanoic acid hydrochloride, methanesulfonate, and toluenesulfonate Samples of 5-amino-4-oxopentanoic acid hydrochloride and toluenesulfonate were weighed and kept in 30 ml plastic cups in a closed chamber at 75-84 relative humidity over saturated ammonium sulfate solution at ambient temperature (ca. 25° C.). The samples were then weighed after different intervals of time to monitor water uptake. The appearance of the samples was also checked at the same time to determine the onset of deliquescence. The results are shown in FIG. 9.

Figure 9:
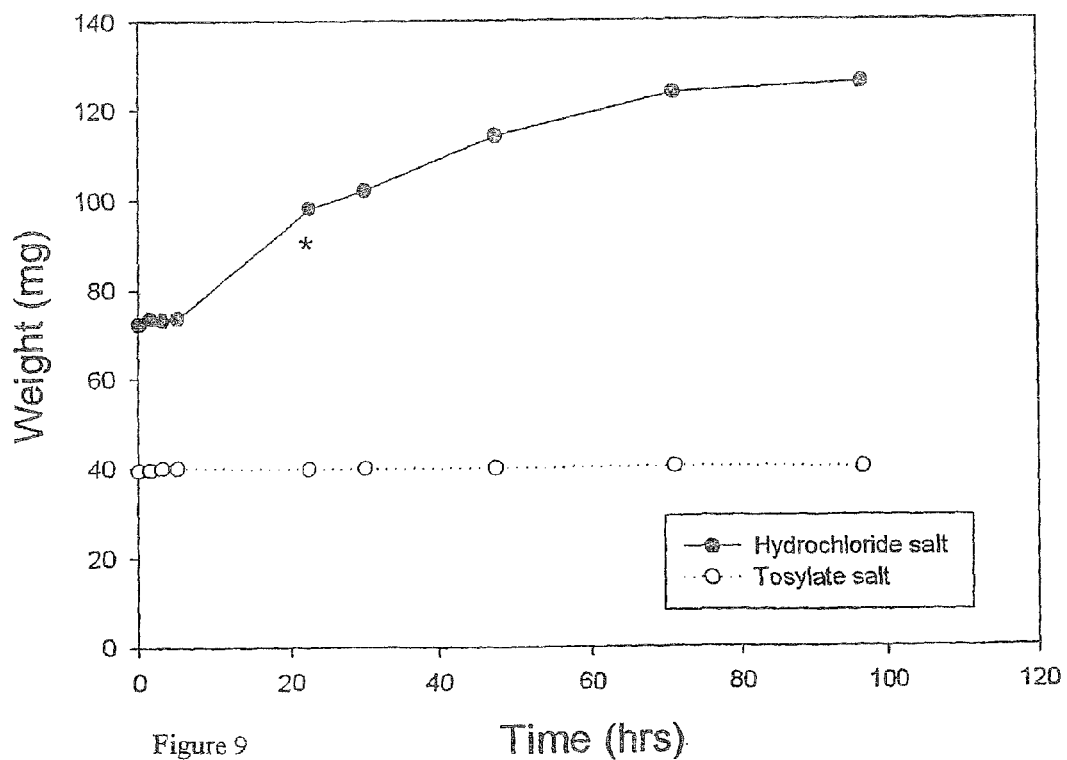
FIG. 9 shows the hygroscopicity of hydrochloride and toluenesulfonate salts of 5-amino-4-oxopentanoic acid.

It can be seen from FIG. 9 that the hydrochloride salt of 5-amino-4-oxopentanoaic acid took up water to a considerable extent as monitored by weight. The onset of deliquescence for the hydrochloride salt occurred after 22.5 hrs (as indicated by an asterisk in the figure). In contrast the tosylate salt did not pick up water and did not change appearance during the test period.

EXAMPLE 42

Hygroscopicity of hexyl 5-amino-4-oxopentanoate hydrochloride, methanesulfonate and toluenesulfonate Samples of hexyl 5-amino-4-oxopentanoate hydrochloride and toluenesulfonate were weighed and kept in 30 ml plastic cups in a closed chamber at 75-84% relative humidity over saturated ammonium sulfate solution at ambient temperature (ca. 25° C.). The samples were then weighed after different intervals of time to monitor water uptake. The appearance of the samples was also checked at the same time to determine the onset of deliquescence. The results are shown in FIG. 10.

Figure 10:
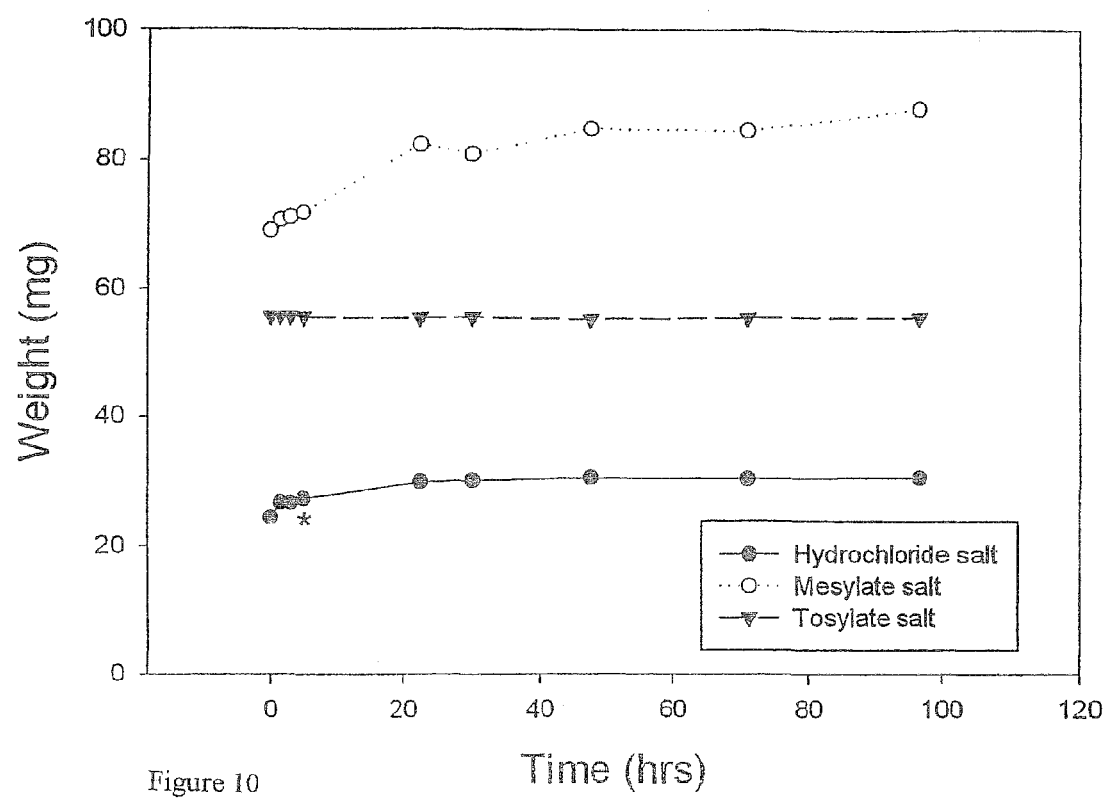
FIG. 10 shows the hygroscopicity of hydrochloride, methanesulfonate and toluenesulfonate salts of hexyl 5-amino-4-oxopentanoic acid.

It can be seen in FIG. 10 that the hydrochloride salt of hexyl 5-amino-4-oxopentanoate did not pick up water to a considerable extent as monitored by weight, but the onset of deliquescence occurred after only 5.0 hrs (as indicated by an asterisk in the figure). The mesylate salt took up water to some extent, but deliquescence did not occur. The tosylate salt of hexyl 5-amino-4-oxolevulinate did not pick up water and did not change appearance during the test period.

The invention claimed is:

1. A method of photodynamic treatment of a disorder or abnormality which is responsive to photodynamic therapy, said method comprising administering to the affected area an acid addition salt of a 5-aminolevulinic acid (5-ALA) ester with an acid selected from nitric acid, sulfonic acid, and a sulfonic acid derivative, wherein the 5-ALA ester is a compound of formula I:

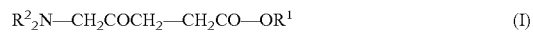

$$R^2{}_2N—CH_2COCH_2—CH_2CO—OR^1 \quad (I)$$

wherein $R^1$ represents a straight-chained $C_{1-6}$ alkyl group optionally substituted by an aryl group, and $R^2$ each independently represents a hydrogen atom or an optionally substituted straight-chained, branched or cyclic alkyl group which may optionally be interrupted by one or more —O—, —NR$^3$—, —S— or —PR$^3$— groups; and $R^3$ is a hydrogen atom or a $C_{1-6}$ alkyl group, optionally together with at least one pharmaceutically acceptable carrier or excipient, and exposing said surfaces to light.

2. The method of claim 1 wherein the light is white light, light in the wavelength region 300-800 nm, or blue light in the wavelength region 380-440 nm.

3. The method of claim 2 wherein said acid is nitric acid and, in formula (I), each $R^2$ represents a hydrogen atom.

4. The method of claim 2, wherein said acid is nitric acid and, in formula (I), $R^1$ is a benzyl or substituted benzyl group.

5. The method of claim 2 wherein said acid is a pharmaceutically acceptable sulfonic acid or sulfonic acid derivative of formula (II):

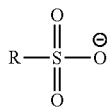
(II)

and, in formula (I), each $R^2$ represents a hydrogen atom.

6. The method of claim 5 wherein R is a hydrogen atom or an optionally substituted alkyl or aryl group.

7. The method of claim 6 wherein $R^1$ is a benzyl or substituted benzyl group.

8. The method of claim 5 wherein $R^1$ represents a straight-chained $C_{1-6}$ alkyl or represents a $C_{1-2}$ alkyl substituted by an aryl group.

9. A method of photodynamic visualization of a disorder or abnormality, said method comprising administering to a site of investigation an acid addition salt of a 5-aminolevulinic acid (5-ALA) ester with an acid selected from nitric acid, sulfonic acid, and a sulfonic acid derivative, wherein the 5-ALA ester is a compound of formula III:

(III)

wherein $R^4$ represents a straight-chained $C_{1-6}$ alkyl group optionally substituted by an aryl group, and $R^5$ each independently represents a hydrogen atom or an optionally substituted straight-chained, branched or cyclic alkyl group which may optionally be interrupted by one or more —O—, —NR$^6$—, —S— or —PR$^6$— groups; and $R^6$ is a hydrogen atom or a $C_{1-6}$ alkyl group, optionally together with at least one pharmaceutically acceptable carrier or excipient, and exposing said surfaces to light.

10. The method of claim 9 wherein the light comprises blue light.

11. The method of claim 10 wherein said acid is nitric acid and, in formula (III), each $R^5$ represents a hydrogen atom.

12. The method of claim 10, wherein said acid is nitric acid and, in formula (III), $R^4$ is a benzyl or substituted benzyl group.

13. The method of claim 10 wherein said acid is a pharmaceutically acceptable sulfonic acid or sulfonic acid derivative of formula (IV):

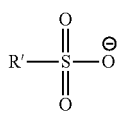
(IV)

and, in formula (III), each $R^5$ represents a hydrogen atom.

14. The method of claim 13 wherein R' is a hydrogen atom or an optionally substituted alkyl or aryl group.

15. The method of claim 14 wherein $R^4$ is a benzyl or substituted benzyl group.

16. The method of claim 13 wherein $R^4$ represents a straight-chained $C_{1-6}$ alkyl or represents a $C_{1-2}$ alkyl substituted by an aryl group.

17. A method of in vitro diagnosis of abnormalities or disorders by assaying a sample of body fluid or tissue of a patient, said method comprising at least the following steps:
  i) admixing said body fluid or tissue with an acid addition salt,
  ii) exposing said mixture to light,
  iii) ascertaining the level of fluorescence, and
  iv) comparing the level of fluorescence to control levels,
  wherein the acid addition salt is an acid addition salt of a 5-aminolevulinic acid (5-ALA) ester with an acid selected from nitric acid, sulfonic acid, and a sulfonic acid derivative, wherein the 5-ALA ester is a compound of formula V:

(V)

wherein $R^7$ represents a straight-chained $C_{1-6}$ alkyl group optionally substituted by an aryl group, and $R^8$ each independently represents a hydrogen atom or an optionally substituted straight-chained, branched or cyclic alkyl group which may optionally be interrupted by one or more —O—, —NR$^9$—, —S— or —PR$^9$— groups; and $R^9$ is a hydrogen atom or a $C_{1-6}$ alkyl group.

18. The method of claim 17, wherein the body fluid or tissue is selected from urine, sputum, blood, semen, tears, spinal fluid, biopsy tissue, and bone marrow.

19. The method of claim 17 wherein the light comprises blue light.

20. The method of claim 19 wherein said acid is nitric acid and, in formula (V), each $R^8$ represents a hydrogen atom.

21. The method of claim 19 wherein said acid is nitric acid and, in formula (V), $R^7$ is a benzyl or substituted benzyl group.

22. The method of claim 19 wherein said acid is a pharmaceutically acceptable sulfonic acid or sulfonic acid derivative of formula (VI):

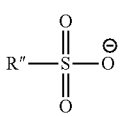
(VI)

and, in formula (V), each $R^8$ represents a hydrogen atom.

23. The method of claim 22 wherein R" is a hydrogen atom or an optionally substituted alkyl or aryl group.

24. The method of claim 22 wherein $R^7$ represents a straight-chained $C_{1-6}$ alkyl or represents a $C_{1-2}$ alkyl substituted by an aryl group.

* * * * *